US011439451B2

(12) United States Patent
Giordano et al.

(10) Patent No.: US 11,439,451 B2
(45) Date of Patent: Sep. 13, 2022

(54) INSERTION APPARATUS FOR AN INTRAMEDULLARY NAIL

(71) Applicant: OrthoPediatrics Corp., Warsaw, IN (US)

(72) Inventors: Michael Giordano, Osceola, IN (US); Chris M. Powers, Warsaw, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 218 days.

(21) Appl. No.: 16/497,716

(22) PCT Filed: Jun. 22, 2018

(86) PCT No.: PCT/US2018/039014
§ 371 (c)(1),
(2) Date: Sep. 25, 2019

(87) PCT Pub. No.: WO2018/237276
PCT Pub. Date: Dec. 27, 2018

(65) Prior Publication Data
US 2021/0068883 A1 Mar. 11, 2021

Related U.S. Application Data

(60) Provisional application No. 62/574,102, filed on Oct. 18, 2017, provisional application No. 62/524,036, filed on Jun. 23, 2017.

(51) Int. Cl.
*A61B 17/92* (2006.01)
*A61B 17/00* (2006.01)

(52) U.S. Cl.
CPC .. *A61B 17/921* (2013.01); *A61B 2017/00469* (2013.01); *A61B 2017/922* (2013.01)

(58) Field of Classification Search
CPC . A61B 17/92; A61B 17/921; A61B 2017/922; A61B 2017/924;
(Continued)

(56) References Cited

U.S. PATENT DOCUMENTS

| 550,879 A | 12/1895 | Golling et al. |
|---|---|---|
| 1,007,824 A | 11/1911 | Trosper |

(Continued)

FOREIGN PATENT DOCUMENTS

| WO | 2006041460 | 4/2006 |
|---|---|---|
| WO | 2011036182 | 3/2011 |
| WO | 2013191819 | 12/2013 |

OTHER PUBLICATIONS

PCT/US2018/039014, Search Report & Written Opinion, 13 pgs dated Sep. 14, 2018.
(Continued)

*Primary Examiner* — Zade Coley
(74) *Attorney, Agent, or Firm* — Gerald W. Roberts; John V. Daniluck; Dentons Bingham Greenebaum LLP

(57) ABSTRACT

A tool for manipulating the position of an implantable medical device. In some embodiments the tool includes a readily releasable grasping feature that securely couples the implant to the tool while the implant is being manipulated. Preferably, the user can simply release the implant from the tool. The tool in other embodiments includes an internal pathway for accommodating non-linear implants, such as curved rods, wires, or nails. In yet other embodiments the tool has multiple handles, each handle being adapted and configured to permit manipulation of the implant in a single predetermined orientation, but with alternative handles for grasping in different hand orientations. Still further embodiments pertain to a kit having a tool and a plurality of collets, each collet being adapted and configured to grasp a different size of implant, but each collet having identical tool cou-
(Continued)

pling features such that any collet in the kit can be used with the single tool. Still further, yet other embodiments pertain to tools having quick release mechanisms for the acceptance or removal of a collet, and some include external features for preventing inadvertent release of the collet when coupled to an implant.

8 Claims, 16 Drawing Sheets

(58) Field of Classification Search
 CPC ........ A61B 2017/925; A61B 2017/927; A61B 2017/928; A61B 17/162; A61B 17/1622; A61B 17/1633; A61B 17/164
 See application file for complete search history.

(56) References Cited

U.S. PATENT DOCUMENTS

| | | | |
|---|---|---|---|
| 1,985,108 A | 12/1933 | Rush | |
| 2,427,128 A | 9/1947 | Ettinger | |
| 2,583,896 A | 1/1952 | Siebrandt | |
| 3,049,018 A | 8/1962 | Lusskin et al. | |
| 4,187,840 A | 2/1980 | Wantanabe | |
| 4,813,407 A | 3/1989 | Vogen | |
| 5,122,146 A | 6/1992 | Chapman et al. | |
| 5,562,357 A | 10/1996 | Sandell | |
| 5,578,032 A | 11/1996 | Lalonde | |
| 5,913,860 A | 6/1999 | Scholl | |
| 6,080,162 A | 6/2000 | Dye et al. | |
| 6,110,179 A | 8/2000 | Flivik et al. | |
| 6,168,595 B1 | 1/2001 | Durham et al. | |
| 6,565,570 B2 | 5/2003 | Sterett et al. | |
| 6,589,241 B1 | 7/2003 | Townsend et al. | |
| 6,610,061 B2 | 8/2003 | Ballier | |
| 6,660,006 B2 | 12/2003 | Markworth et al. | |
| 6,689,140 B2 | 2/2004 | Cohen | |
| 7,722,625 B2 | 5/2010 | Sanders et al. | |
| 7,744,598 B2 | 6/2010 | Brumfield et al. | |
| 7,776,040 B2 | 8/2010 | Markworth et al. | |
| 8,096,996 B2 | 1/2012 | Gutierrez et al. | |
| 8,235,997 B2 | 8/2012 | Hoffman et al. | |
| 8,308,774 B2 | 11/2012 | Hoffman et al. | |
| 8,685,037 B1 | 4/2014 | Jordan | |
| 8,900,240 B2 | 12/2014 | White | |
| 8,939,977 B2 * | 1/2015 | DiPoto | A61B 17/7097 606/63 |
| 8,986,306 B2 | 3/2015 | Wright et al. | |
| 8,998,906 B2 | 4/2015 | Kirschman | |
| 9,241,807 B2 | 1/2016 | Mohar et al. | |
| 9,301,853 B2 | 4/2016 | Richter et al. | |
| 2002/0072753 A1 | 6/2002 | Cohen | |
| 2003/0199872 A1 | 10/2003 | Markworth | |
| 2005/0049629 A1 | 3/2005 | Koo | |
| 2005/0055031 A1 | 3/2005 | Lim | |
| 2005/0113832 A1 | 3/2005 | Molz et al. | |
| 2005/0273102 A1 | 12/2005 | Powell et al. | |
| 2006/0004379 A1 | 1/2006 | Sanders | |
| 2007/0219582 A1 | 9/2007 | Brunelle et al. | |
| 2008/0097436 A1 * | 4/2008 | Culbert | A61B 17/1757 606/86 A |
| 2008/0308600 A1 | 12/2008 | Kana | |
| 2010/0137889 A1 | 6/2010 | Oren et al. | |
| 2011/0106183 A1 | 5/2011 | Dell'oca | |
| 2013/0116693 A1 | 5/2013 | Nelson et al. | |
| 2013/0116733 A1 | 5/2013 | Stoll, Jr. | |
| 2013/0345762 A1 | 12/2013 | Dell'oca | |
| 2015/0025582 A1 | 1/2015 | Zalenski | |
| 2016/0157871 A1 * | 6/2016 | Overes | A61B 17/88 29/428 |

OTHER PUBLICATIONS

PCT/US2018/039014, International Preliminary Reporton Patentability, IB Officer Agnes Wittman-Regis, ISA/US—Lee W. Young, 8 pages dated Jan. 2, 2020.
DePuy Synthes Trauma, Suprapatellar Instrumentation for Titanium Cannulated Tibial Nails, 83 pgs. Jan. 1, 2013.
Stryker®, Implant Extraction Set, 4 pgs May 1, 2014.
Stryker®, Implant Extraction Set Quick Reference Guide, 8 pgs 00 Jan. 2008.
Stryker®, Osteosynthesis—Implant Extraction Set, 20 pgs 00 Jan. 2009.
Stryker®, T2 Kids Flexible Intramedullary Nails: Forearm Midshaft Technique, 1 pg. 00 Jan. 2011.
Stryker®—T2Kids Flexible Nailing System, 1 pg 00 Jan. 2013.
Stryker®—Femoral Nailing System Operative Technique, 42 pgs 00 Jan. 2005.
Synthes®—Small Universal Chuck with T-Handle, 2 pgs. 00 Jan. 2003.

* cited by examiner

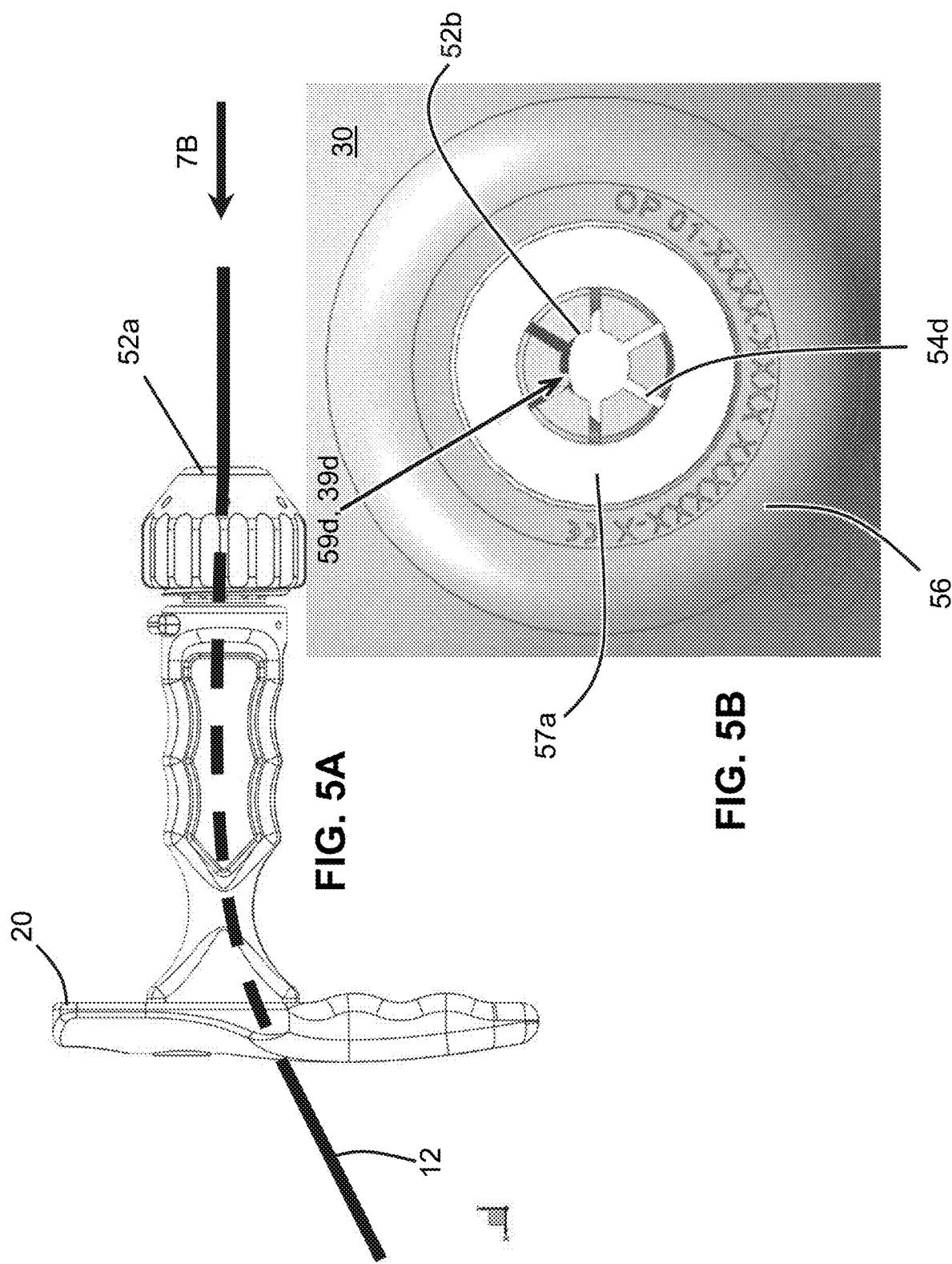

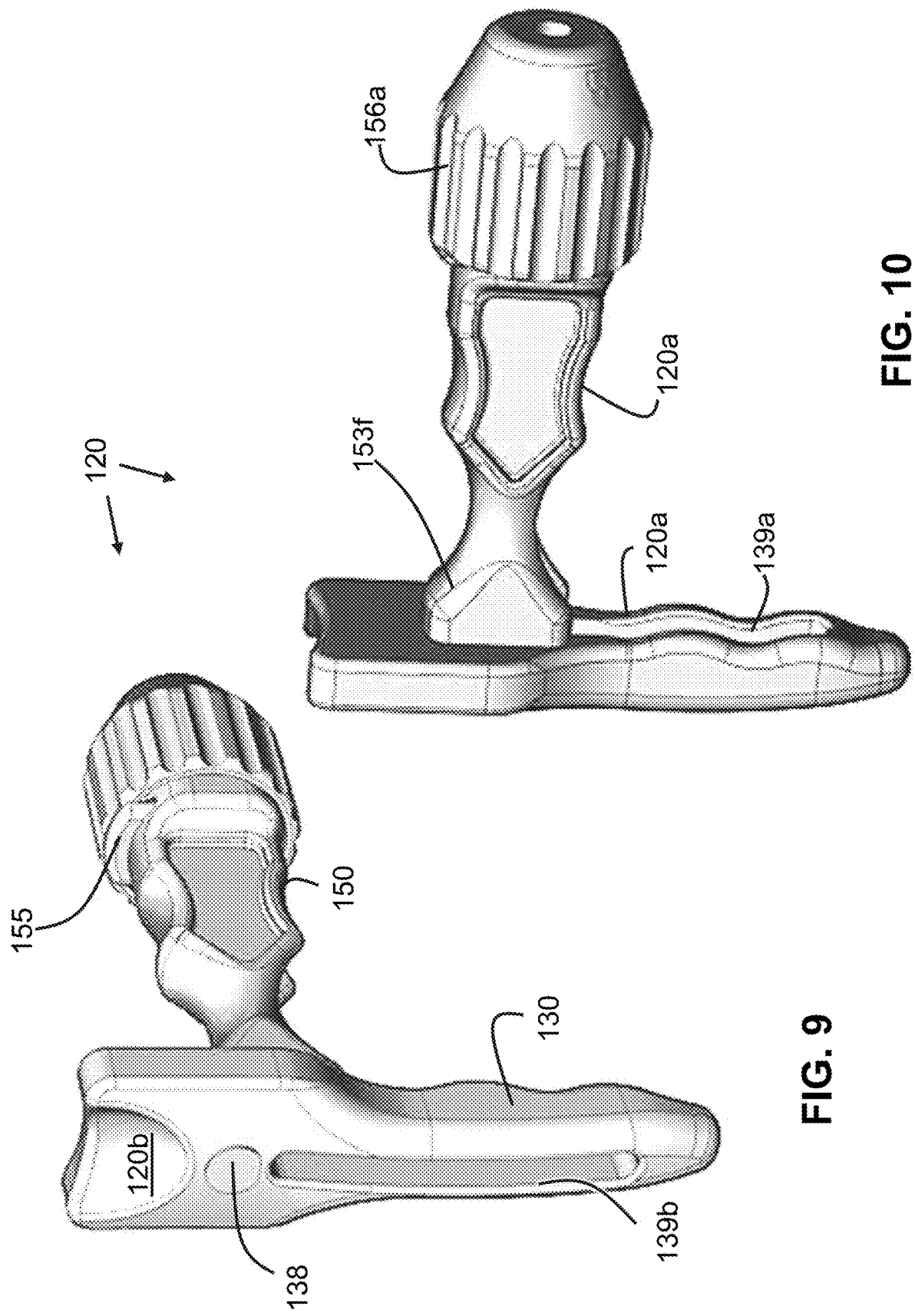

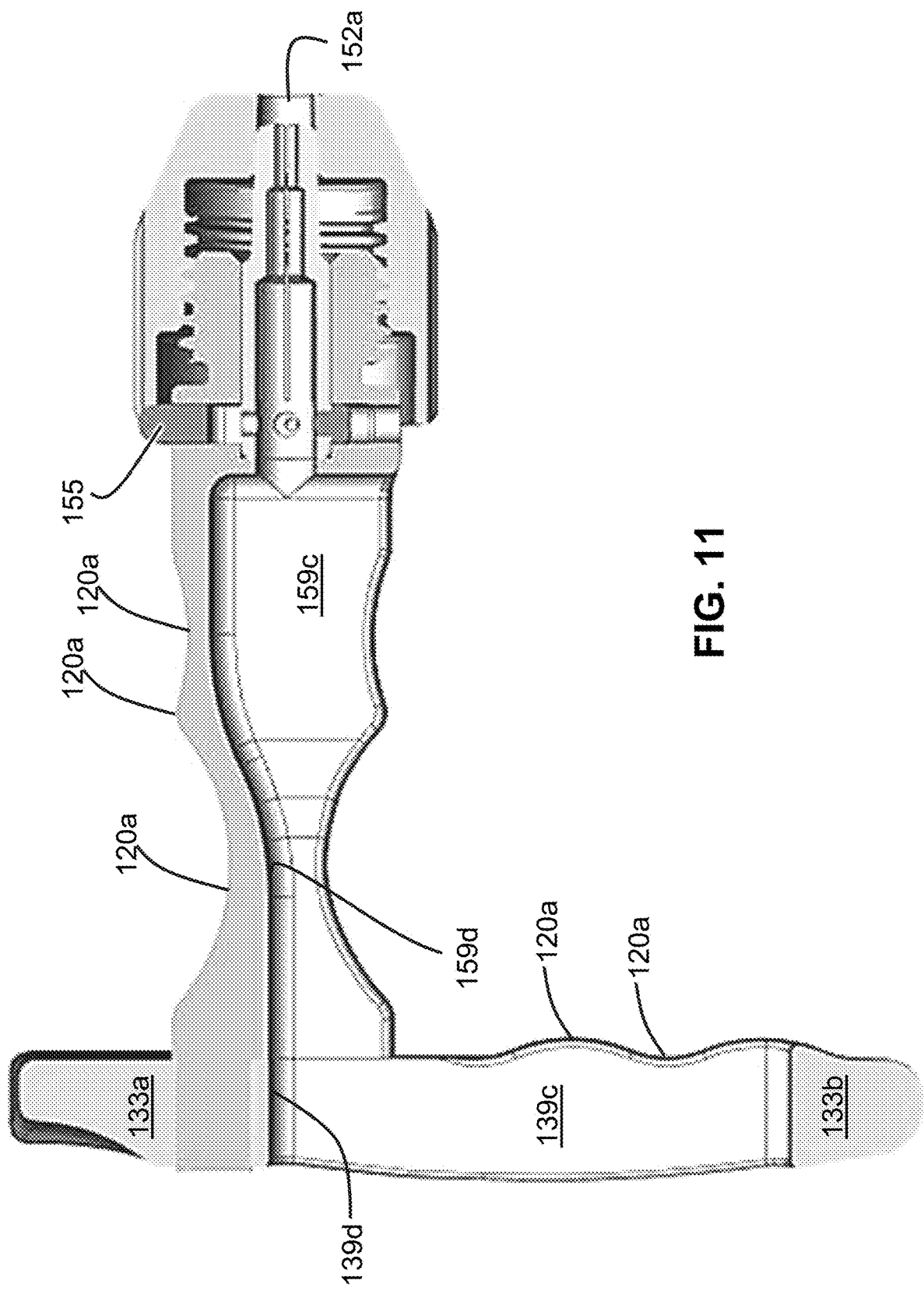

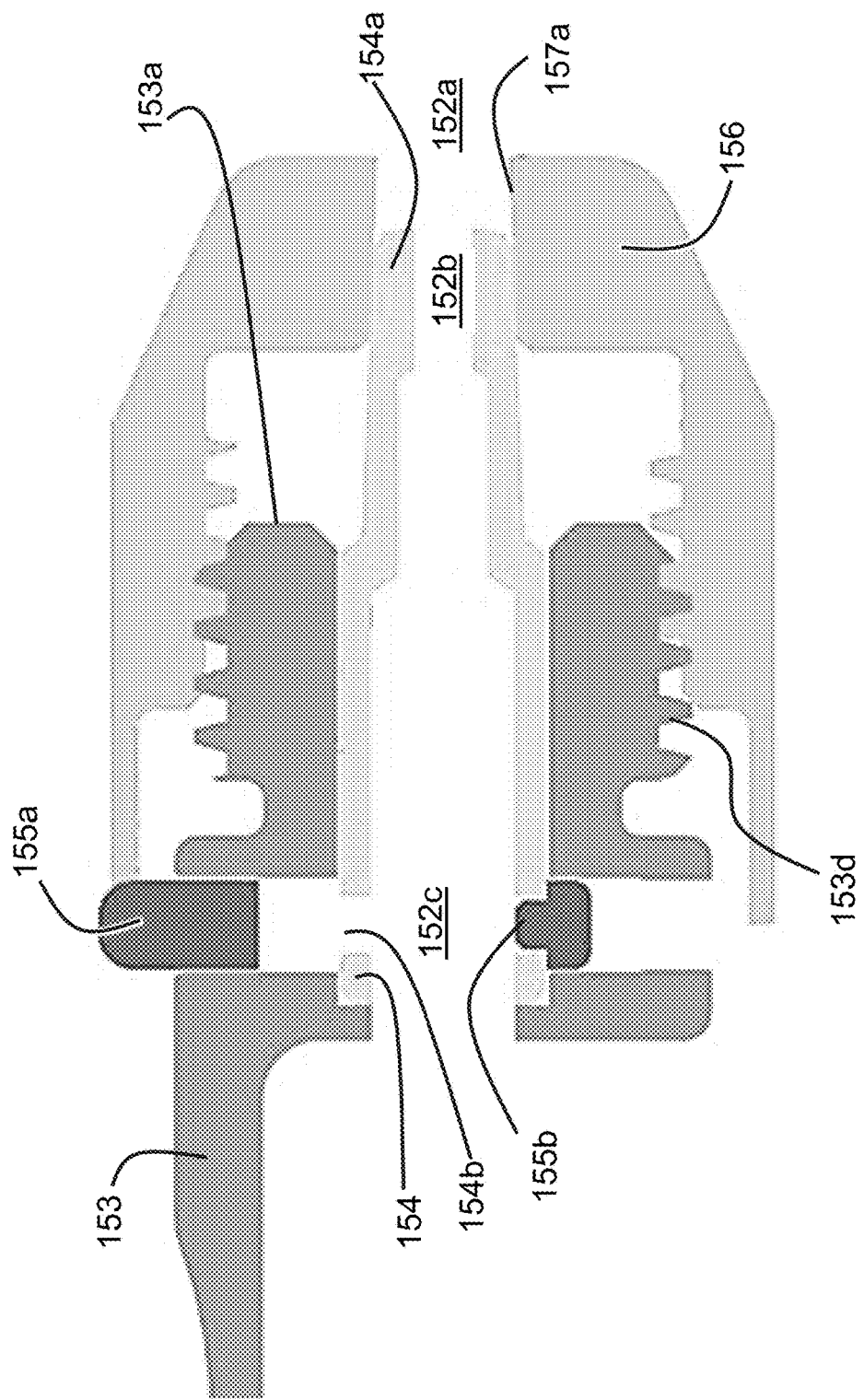

INSERTION APPARATUS FOR AN INTRAMEDULLARY NAIL

CROSS REFERENCE TO RELATED APPLICATION

This application is a national stage filing of International Patent Application Serial No. PCT/US2018/039014, filed Jun. 22, 2018, which claims the benefit of priority to U.S. Provisional Patent Application Ser. No. 62/524,036, filed Jun. 23, 2017, and U.S. Provisional Patent Application Ser. No. 62/574,102, filed Oct. 18, 2017, both of which are incorporated herein by reference.

FIELD OF THE INVENTION

The present invention pertains to devices for manipulating orthopedic implants, and in particular to devices and methods for manipulation of intramedullary nails.

SUMMARY OF THE INVENTION

Some aspects of the various embodiments shown herein pertain to a tool for manipulating an implantable medical device within a biological unit.

Different aspects of yet other embodiments pertain to tools that have multiple handles for manipulating an implant while maintaining a single predetermined orientation of the implant relative to the biological unit. Preferably, each of the handles permit different hand and wrist orientations for the user, each of the handles and orientations including ergonomic considerations for secure grasping.

Yet other aspects of different embodiments are adapted and configured to receive implants such as rods, rod assemblies, wires, nails, or the like, that have cylindrically shaped surfaces suitable for frictional grasping within a chuck or collet.

In still further embodiments, various aspects pertain to securement of the tool to implants of various configurations, including, by way of example only, relatively straight rods or bent rods.

In still further embodiments, various aspects pertain to multi-position release mechanisms that permit easy removal of a collet from the tool, yet also permitting easy securement of the collet to the tool.

In still other embodiments, various aspects pertain to safety features that prevent the inadvertent release of the secured implant from the tool.

BRIEF DESCRIPTION OF THE DRAWINGS

Some of the figures shown herein may include dimensions. Further, the figures shown herein have been created from scaled drawings, and scaled models. It is understood that such dimensions, or the relative scaling within a figure, are by way of example, and not to be construed as limiting unless so stated in a claim.

FIG. 5A is a side elevational view of the apparatus of FIG. 1 indicating one path for an intramedullary nail.

FIG. 5B is a view down the internal channel of the apparatus of FIG. 5A as viewed from arrow 7B, with the intramedullary nail removed.

FIG. 9 is a side, proximal, perspective view of a shaded line drawing from a scaled CAD model of an apparatus according to another embodiment of the present invention.

FIG. 10 is a side, distal perspective view of the apparatus of FIG. 9.

FIG. 11 is a side elevational cross sectional view of the apparatus of FIG. 9.

FIG. 12 is a close-up cross sectional view of a portion of the apparatus of FIG. 11.

ELEMENT NUMBERING

Figure 1:
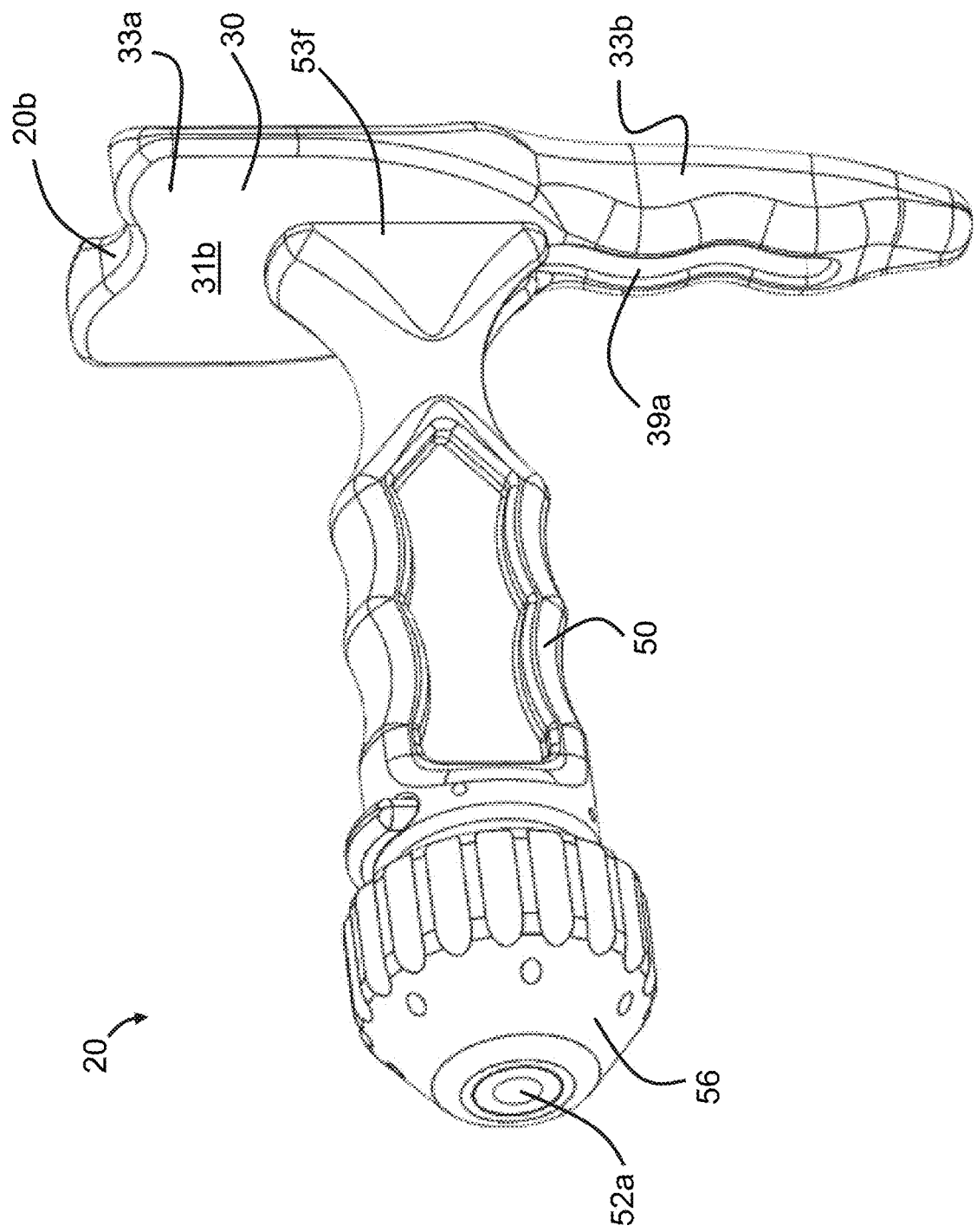
FIG. 1 is a side perspective line drawing from a scaled CAD model of an apparatus according to one embodiment of the present invention.

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

12 intramedullary nail
16 defined cylinder
17 interfering wall
20 inserter
  a finger grips; ridges, valleys
  b thumb depression; indentation
30 vertical handle; impaction handle; second handle; second member
31 mallet surfaces
  a insertion surface
  b extraction surface
33 vertical body
  a upper section; top
  b lower section; bottom
38 threaded hole
39 slot; aperture; portal
  a exit; portal -continued b  entrance; portal
  c  internal passage; internal cavity
  d  Interfering section; intersecting section; internal wall
50  horizontal handle assembly; first handle; first member
52  internal channel
  a  exit; portal
  b  chucking portion
  c  entrance; portal
  d  shading
53  horizontal body
  a  front face
  b  lightening passage
  c  retention or driving pocket; complementary non-circular shape
  d  external threads
  e  channel
  f  base
54  collet; chuck
  a  compressible diametral section
  b  pockets
  c  driven or orienting section; complementary non-circular shape
  d  slits
55  retention mechanism
  a  slide; push button
  b  protrusion; 1$^{st}$ mating feature
  c  spring
56  knob
  a  outer gripping surface
  b  internal threads
  c  raceway
  d  proximal end
  e  cavity
  f  inner compression surface
57  compression assembly
  a  sliding compression member collar
  b  sliding compression member flange
  c  ball race
  d  balls
  e  snap ring
  f  inner compression surface
59  slot; aperture
  a  exit
  b  entrance
  c  internal passage; internal cavity; part of internal channel
  d  Interfacing section; intersecting section; internal wall

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments, it therefore being understood that use of the word "preferably" implies the term "optional."

The use of an N-series prefix for an element number (NXX.XX) refers to an element that is the same as the non-prefixed element (XX.XX), except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology. Further, it is understood that the features 1020.1 and 20.1 may be backward compatible, such that a feature (NXX.XX) may include features compatible with other various embodiments (MXX.XX), as would be understood by those of ordinary skill in the art. This description convention also applies to the use of prime ('), double prime ("), and triple prime ("') suffixed element numbers. Therefore, it is not necessary to describe the features of 20.1, 20.1', 20.1", and 20.1'" that are the same, since these common features are apparent to persons of ordinary skill in the related field of technology.

This document may use different words to describe the same element number, or to refer to an element number in a specific family of features (NXX.XX). It is understood that such multiple usage is not intended to provide a redefinition of any language herein. It is understood that such words demonstrate that the particular feature can be considered in various linguistical ways, such ways not necessarily being additive or exclusive.

Various embodiments of the present invention pertain to tools for manipulation of orthopedic implants, especially during surgical procedures. As one example, various embodiments provide an effective and easily controllable handle for manipulation of an implant that is frictionally retained by the tool. As examples, the tools shown herein are appropriate for frictional retention of devices such as intramedullary nails, screws, rods, wire, and the like.

The various embodiments shown and discussed herein include an adjustable collet or chuck that the user (such as an orthopedic surgeon) can adjust to provide a firm, reliable grip onto the implant, and manipulate the implant, such as for insertion or extraction, by means of one or more ergonomic handles. In some embodiments, the tool includes vertical and horizontal handles, each handle being provided with means for gripping of the handle by the user's fingers and/or thumb.

In some embodiments, the two handles are generally orthogonal to one another, in an approximate T-shape or L-shape. It is preferred that the two handles are rigidly coupled to one another, such as by being provided integrally in a unitary body, by means of welding, fastening, brazing, or similar methods.

In some embodiments, the tool includes a handle that is generally aligned with the direction in which the implant (such as an intramedullary nail) is introduced into the biological unit. The hand gripping features of this handle provide an orientation for the users hand in which at least a portion of the implant (such as the frictionally constrained end of the intramedullary nail) are arranged such that one or more of the fingers of the user wrap around the axis of the constrained portion. This handle preferably and optionally includes at least a portion of the internal channel that receives the implant, it being understood that this internal channel can be a pathway that is included within this handle, but can also be considered as part of the collet or other features that are part of a horizontal handle assembly.

In one embodiment, the tool can be frictionally affixed to the implant, and the user can manipulate the implant by either of the handles. By using the vertical handle, the user's hand is roughly orthogonal to the axis along which the implant is affixed. If during the medical procedure it becomes more effective for the user to reorient his grip relative to the affixed implant, then it is possible for the user to simply switch the gripping hand from the vertical handle to the horizontal handle.

In other embodiments, the two handles are attached to one another in fixed relationship. Still further in other embodiments, this fixed relationship is in the shape of an offset T-shape, such that the portion of the vertical handle below the junction with the horizontal handle is longer than the portion of the vertical handle that is above this junction. Preferably, this longer, lower portion of the vertical handle ergonomically accepts the four wrapped fingers of the user, with the user's thumb being positioned to contact the top surface of the upper vertical portion. This manner of ergonomic fit is more reliable than other types of vertical handles, especially those handles in which the vertical handle is a simple rod that slides through a hole in the horizontal handle.

Yet another aspect of some embodiments of the tool pertain to the tool's accommodation of nonlinear or bent or curved implants, such as a nonlinear intramedullary nail. The tool can provide internal cavities in one or both of the handles in which the proximal extension of the implant (i.e. from the collet toward the user's hand) can be accommodated. Preferably, each of the two handles include such cavities, and further include lengthwise slots that open from the cavity to ambient conditions.

In still further embodiments, the cavities are adapted and configured such that a straight implant can be elastically brought to bear against an internal wall when the implant is retained in the collet. In such embodiments, this internal wall, being slightly offset from an otherwise straight line path through the collet, provides for a frictional force of the implant against the internal wall such that the portion of the implant extending proximally toward the user is held firmly in place by friction from the elastic deformation, and therefore not permitted to wiggle as the implant is manipulated.

In yet other embodiments a bent or non-linear nail can be accommodated through an entrance in the vertical handle that is slotted. In such cases with bent nails, a generally straight, approximately linear portion of the nail can be constrained by a collapsible collet at the exit of an internal channel, with the remainder of the bent section being accommodated through this slotted entrance (i.e., the entrance being proximate to the user holding the vertical handle). Preferably, at least a portion of this entrance slot is aligned with the centerline of the channel exit, such that a straight nail or other type of implant can be accommodated.

Still further embodiments pertain to tools that are adapted and configured to be provided with a kit of different size collets. Each of the collets have different internal sizes that are adapted and configured for frictional grasping of different outer diameters of implants. However, the external geometry of at least one end of the collet is maintained at a common size and shape within the kit. This end is adapted and configured to be received within a pocket of one of the handles. Preferably this interfacing end of the collet and the pocket of the handle are of complementary, non-circular geometry, such that the collet is not permitted to rotate relative to the pocket.

In still further embodiments, the internal collet of the tool is repeatedly releasable and replaceable within the handle. A handle of the tool preferably includes a mechanism that the user can easily actuate from one position in which the collet is retained within the handle, to another position in which the collet can easily be removed from the handle. In one embodiment, this retention mechanism includes a radially sliding push button that moves a small protrusion either into or out of a corresponding hole in the collet. However, various other embodiments of the present invention contemplate other configurations of retention mechanisms, including those having an axially sliding or circumferentially sliding button or lever, and the like.

A still further aspect of some embodiments pertains to the management of any torque that is applied to the implant during a hand-adjustable frictional coupling of the implant to the collet. In some embodiments, the tool includes a hand-adjustable knob proximate to the distal end of the tool, and which is rotatably received by threads at the distal end of a handle. As this knob is tightened by way of a threaded coupling, the knob likewise moves axially. By way of a tapered interface and elastically flexible collet, this axial movement of the knob relative to the collet accomplishes a radially-directed closure of a flexible part of the collet around the implant. This radially-directed movement (and load) provides the frictional coupling of the implant to the assembled tool. However, the rotation of the knob likewise provides a frictional torque against the outer diameter of the implant, which may be undesirable if the distal end of the implant is located within the patient. In order to manage and reduce this frictional torque, some embodiments include a low-friction torqueing interface of the knob against the collet. The friction of this interface can be managed with, as examples, ball bearings, roller bearings, low friction washers, low friction coatings, low friction materials, and the like.

Figure 2:
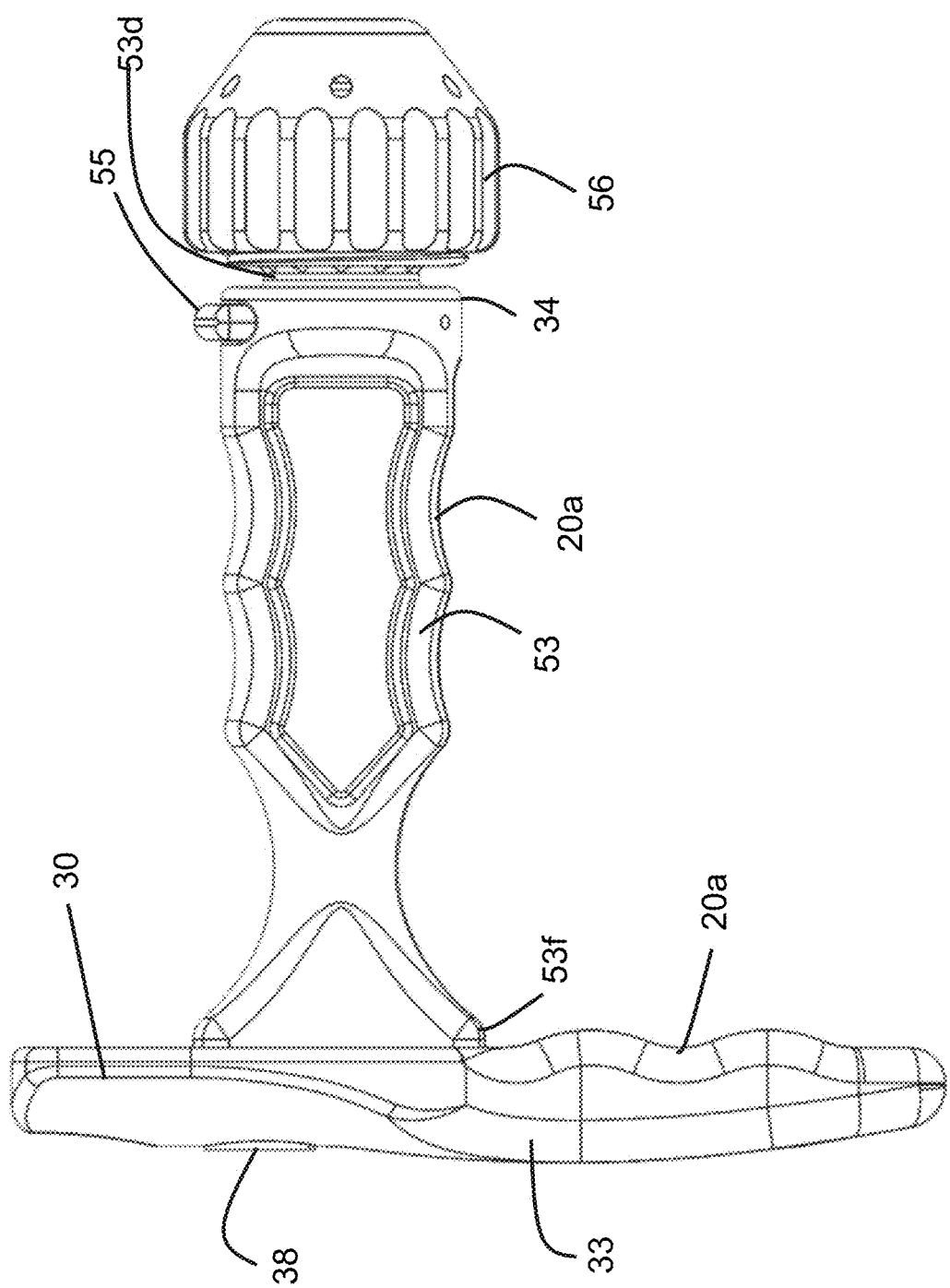
FIG. 2 is a side elevational view of the opposite side of the apparatus of FIG. 1, FIG. 2 being presented with consistent relative scaling for one embodiment of the present invention.
Figure 3:
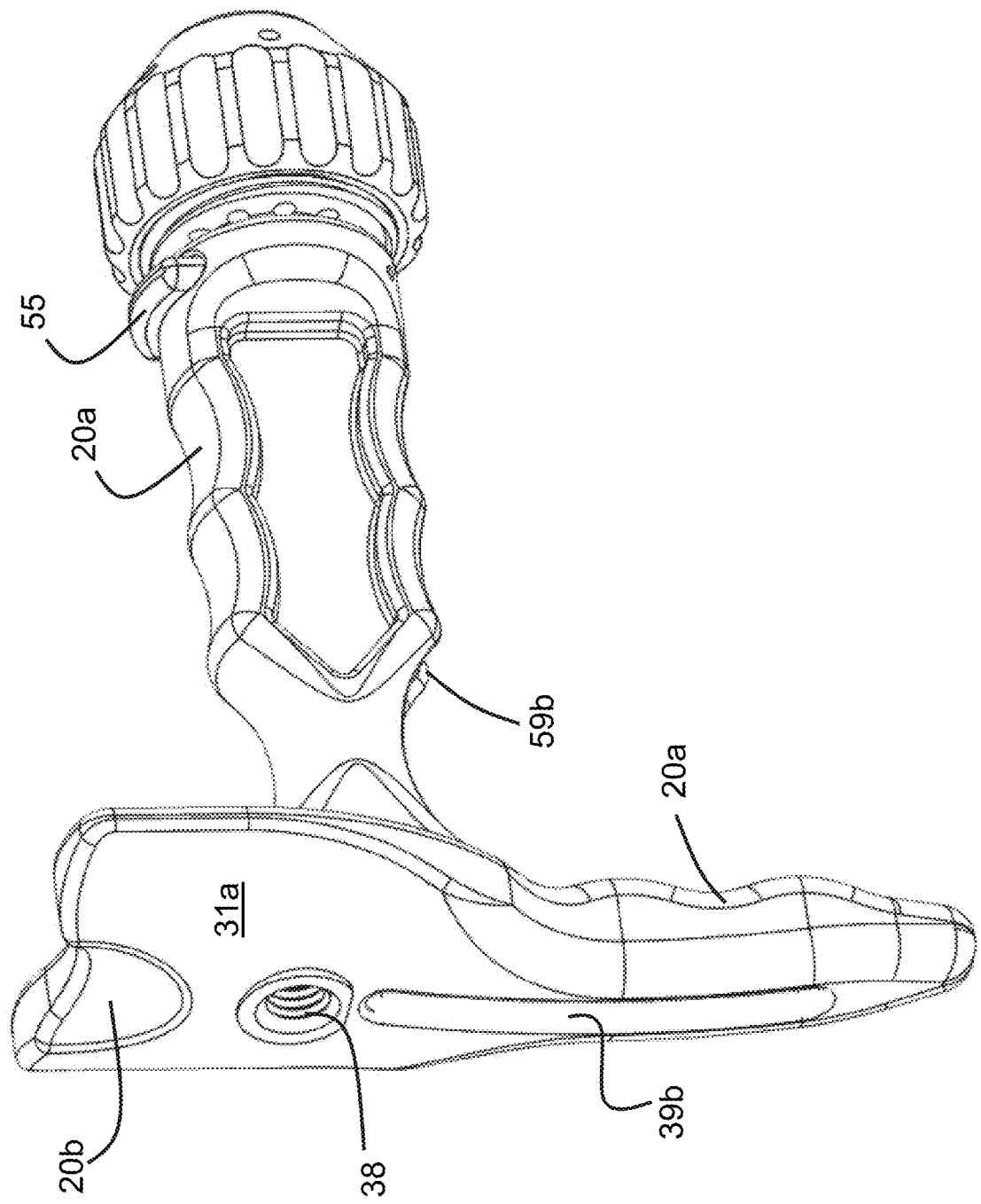
FIG. 3 is a side, proximal, perspective view of the apparatus of FIG. 2.

FIGS. 1, 2, and 3 show various external views of an apparatus 20 according to one embodiment of the present invention. Apparatus 20 is useful in the manipulation of medical implants during surgery, especially for insertion and extraction of intramedullary nails. However, the inventions discussed herein have application beyond manipulation of intramedullary nails or other implants, and further have application outside of the field of medicine.

Figure 4:
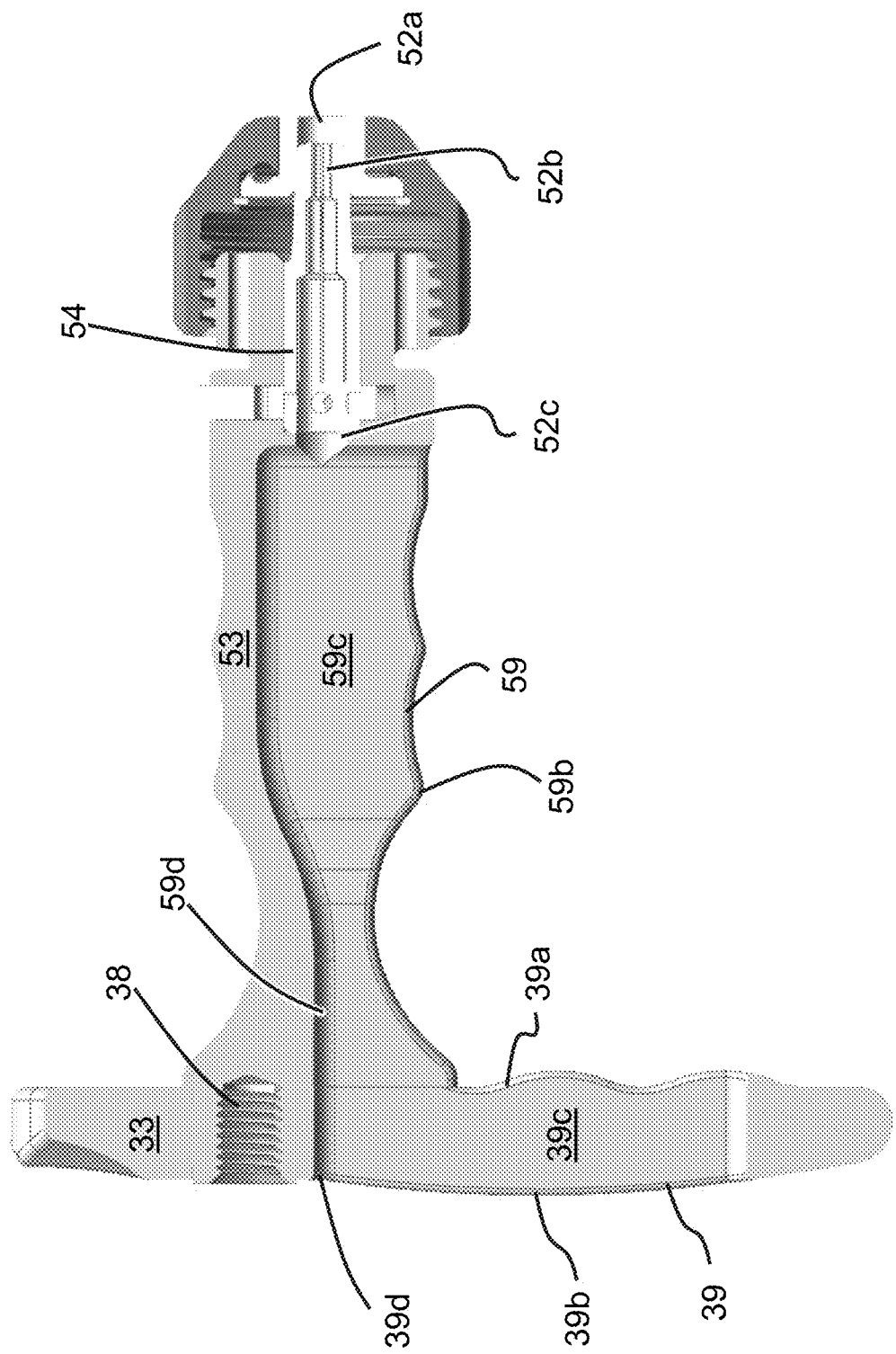
FIG. 4 is a cross sectional view of the apparatus of FIG. 2.

Apparatus 20 includes a horizontal handle assembly 50 extending from the distal side of a vertical handle 30. Preferably, horizontal handle assembly 50 includes a horizontal body 53 (as best seen in FIG. 4) that is unitary with a vertical body 33. Vertical and horizontal bodies 33 and 53, respectively, are arranged in an approximate T-shape. It can be seen that the widened base 53*f* of body 53 generally subdivides body 33 into an upper portion 33*a* located above base 53*f*, and a lower portion 33*b* located on the opposite side of base 53*f*.

Bodies 33 and 53 are adapted and configured to be gripped by the hand of a user. Referring to FIG. 2, it can be seen that vertical body 33 includes a plurality of ridges or finger grips 20*a*. Likewise, horizontal body 53 includes a plurality of ridges, valleys, and/or combinations of ridges and valleys useful as finger grips 20*a*. Vertical handle 30 is adapted and configured to be gripped by the hand of a user, with the fingers extending around grips 20a and below base 53f of body 53 in lower portion 33b. The thumb of the user can be placed in a thumb depression 20b located at the top of body 33 and above base 53f in upper portion 33a.

These gripping features of vertical handle 30 are adapted and configured for manipulation by the user of an intramedullary nail extending out of channel exit 52a and extending into the bone of the recipient. Apparatus 20 further includes the gripping features 20a on body 53 as previously described, which likewise facilitate manipulation of an intramedullary nail extending out of exit 52a and into the bone of the recipient. Various embodiments of the present invention contemplate an apparatus such as apparatus 20 that can maintain the medical implant (such as the IM nail) in a predetermined position or orientation (esp., relative to the recipient), which allowing the user to use either the horizontal body finger grips, or the vertical body finger grips.

Vertical body 33 further includes features adapted and configured to receive impacts from a mallet or hammer. The user can strike insertion surface 31a to further drive the IM nail in a distal direction. Further, extraction of the nail (movement toward the proximal direction) can be accomplished by impacts to extraction surface 31b.

Insertion and extraction of the IM nail can also be accomplished with a slap hammer. The threaded end of the slap hammer can be coupled to threaded hole 38 located on the proximal side of body 33. Referring to FIG. 4, it can be seen that threaded coupling 38 is located proximate to the widened base portion 53f of body 53, so as to provide a suitable load path into body 33 with appropriate management of the stresses imposed by the slap hammer. In still further embodiments, the axis of threaded hole 38 is aligned generally with the axis of the internal channel 52. In some embodiments, these two axes are generally co-incident. As shown in FIG. 4, the axis of coupling 38 is located above the axis of channel 52, yet other embodiments contemplate the axis of the threaded hole 38 being located below the axis of the internal channel.

Vertical handle 30 further includes an elongated slot or aperture 39, as best seen in FIGS. 1 and 3. Slot 39 includes an entrance 39b into a cavity 39c within body 33, this cavity being best seen in FIG. 4. In some embodiments, this internal cavity 39c further includes an exit 39a, as best seen in FIG. 1. Slot 39 provides a pathway for the proximal end of an IM nail, as will be described in more detail.

Figure 5C:
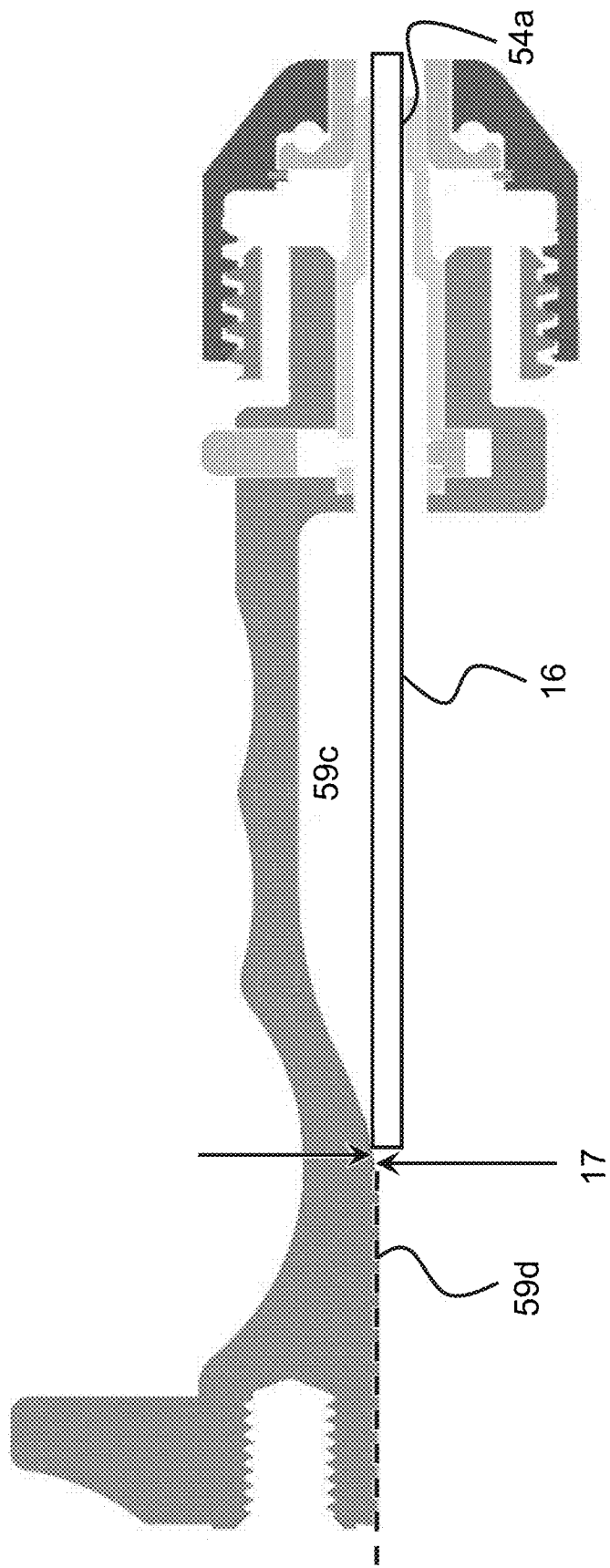
FIG. 5C is a partial cross sectional side view of the apparatus of FIG. 4.

Some embodiments of the present invention include apparatus and methods for securely retaining and manipulating a bent or non-linear portion of an intramedullary nail. FIGS. 4, 5A, 5B, and 5C show some of the features of device 20 that pertain to this capability. Referring first to FIG. 5A, it can be seen that a bent IM nail 12 can be accommodated within apparatus 20. The IM nail 20 extends out of the exit 52a of an internal channel 52. Immediately upstream (proximal) from exit 52a is a chucking or grasping portion 52b formed by a collet 54 as will be explained later. Channel 52 extends into an internal cavity 59c within the body 53 of horizontal handle assembly 50.

As best seen in FIG. 4, this internal cavity 59c extends from entrance 52c to entrance 39b of slot 39 in body 33. The underside of cavity 59c is open through a bottom side entrance 59b of a downward facing slot 59. Internal cavity 59c interconnects with a cavity 39c located generally between exit 39a of slot 39 and entrance 39b. Referring again to FIG. 5A, it can be seen that the non-linear portion of an IM nail can extend within these internal cavities 59c and 39c. Referring to FIGS. 5A and 4, it can be seen that IM nail 12 is positioned by the user at the entrance 39b of slot 39. Portions of the IM nail may or may not extend from exit 39a of slot 39, or simply pass into slot 59. As FIG. 4 shows, the IM nail may pass directly from entrance 39b into cavity 59c (such as near the upper, inner wall 39d), or the IM nail may pass through a lower portion of entrance 39b, through exit 39a, and subsequently through entrance 59b into cavity 59c. The IM nail enters the internal channel 59c, extends through chucking portion 59b, and extends out of exit 52a for subsequent placement into the recipient.

Some embodiments of the present invention include a further feature for the positive control and manipulation of an IM nail, as best seen in FIGS. 5B and 5C. FIG. 5C shows an imaginary cylinder 16 that extends in a linear fashion from the chucking portion 52b of channel 52. Defined cylinder 16 is shown having a constant diameter, the diameter being consistent with the diameter of the chucking portion 52b. It can be seen that this cylinder will extend through a portion of cavity 59c, but begins to overlap with an internal wall 59d of slot 59, as indicated in FIG. 5C by the two arrows. The top arrow indicates the portion of internal wall 59b where the upper boundary of the cylinder would make contact. The lower arrow depicts the internal wall 59d that extends within the entrance to channel 59c. This "shadowing" of the diameter established by chucking portion 52b by the internal walls 39d and 59d can be seen in FIG. 5B.

Some embodiments of the present invention include this interference between the internal walls of the cavity and the straight line path of the chucking portion in order to more effectively grip and retain the straight portion of an IM nail. In some applications, this slight interference prevents the proximal end of the IM nail from moving back and forth ("wiggling" relative to bodies 53 and 33) as the IM nail is manipulated into the intramedullary channel.

Figure 6:
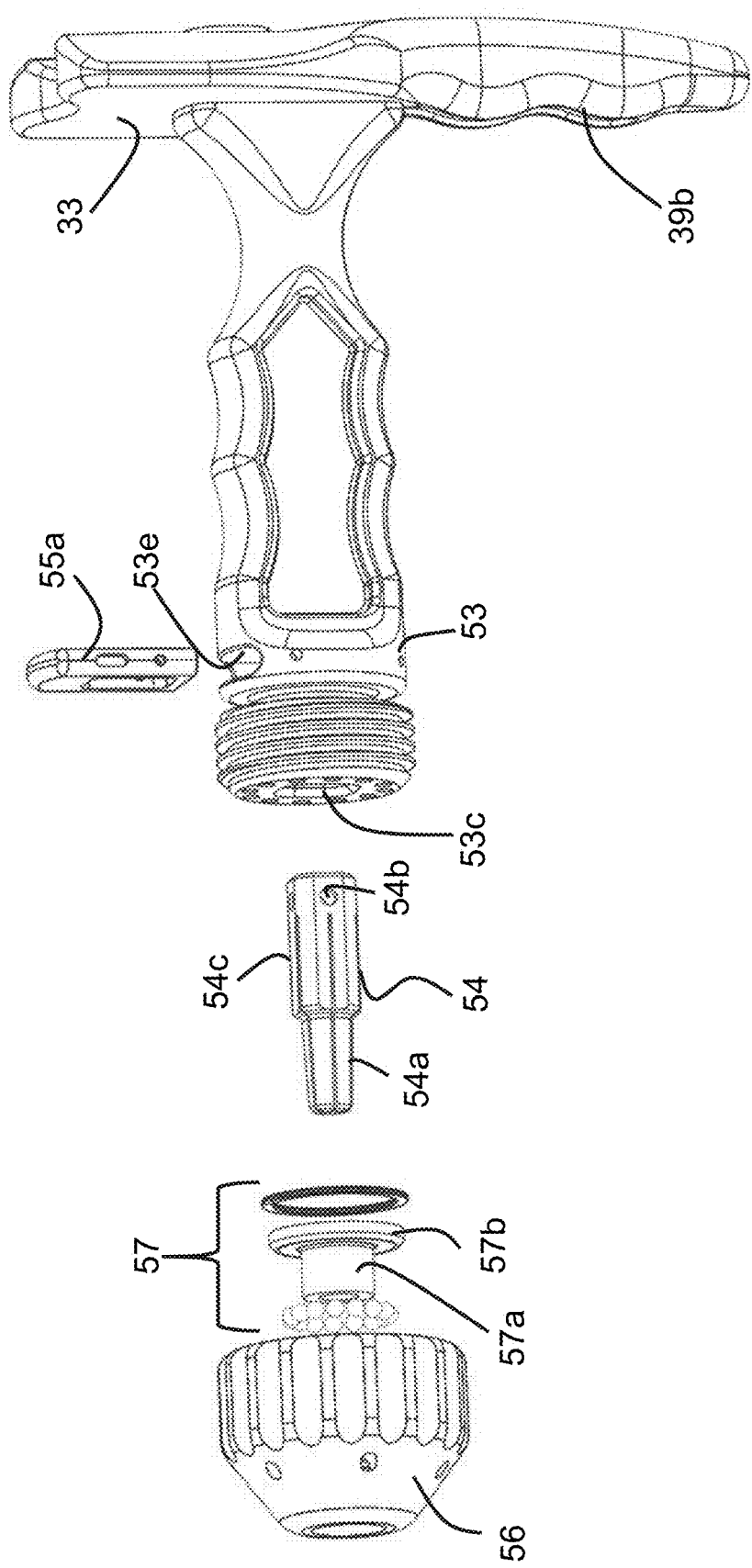
FIG. 6 is a side, perspective, exploded view of the apparatus of FIG. 1.
Figure 7:
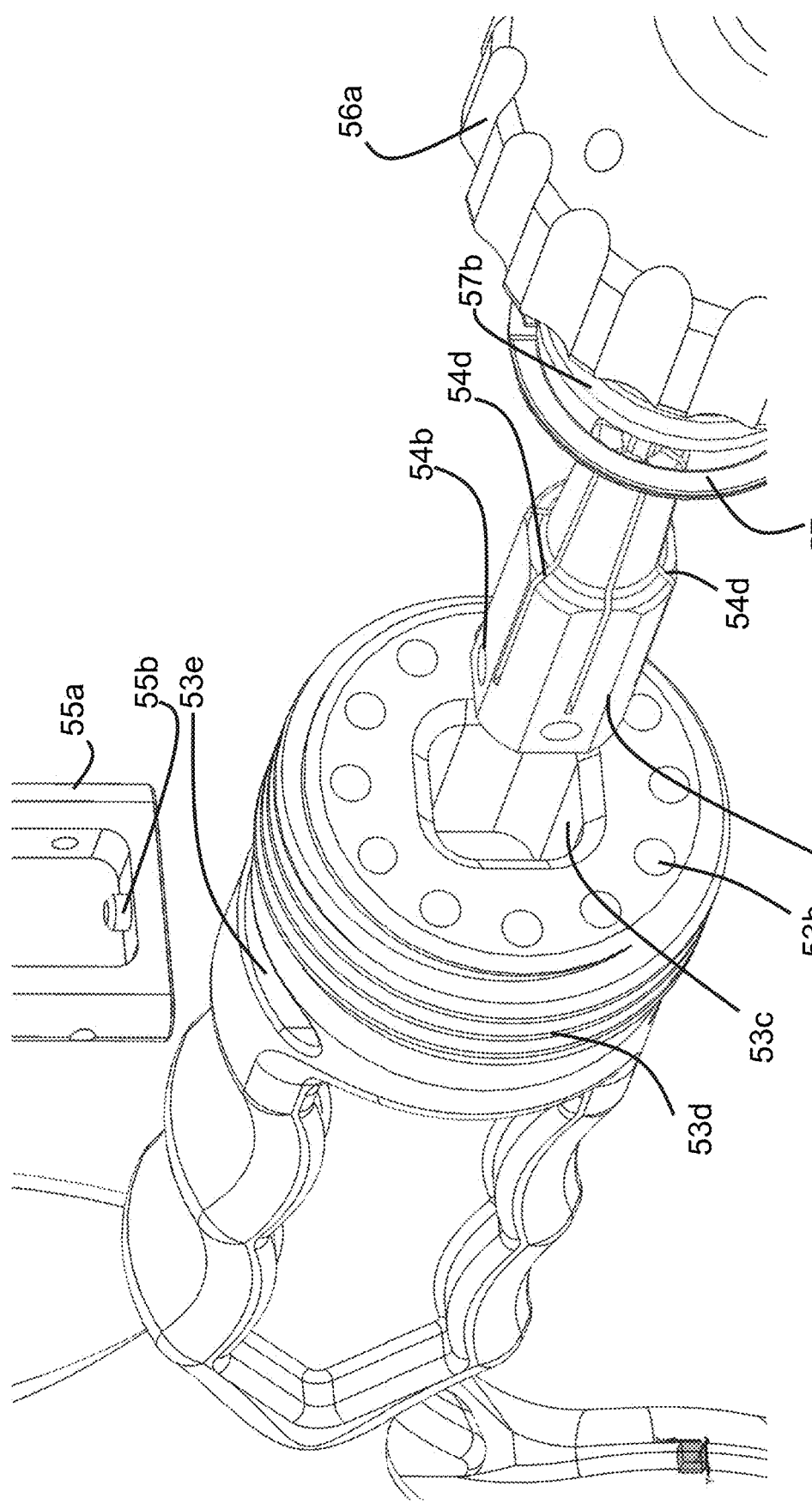
FIG. 7 is an exploded close-up view of a portion of the apparatus of FIG. 1.
Figure 8:
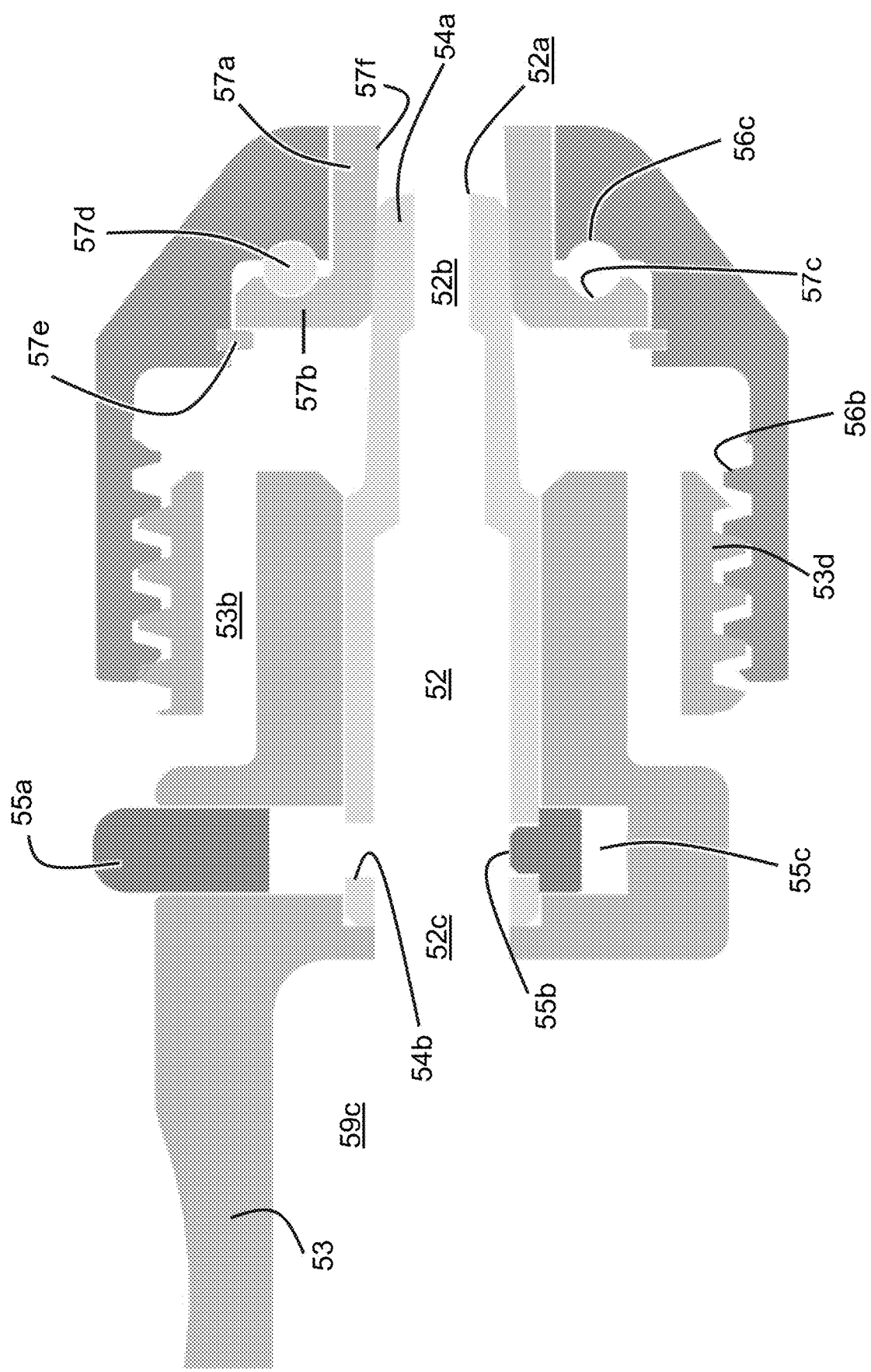
FIG. 8 is a cross-sectional representation of a portion of the apparatus of FIG. 1, FIG. 8 being presented with consistent relative scaling for one embodiment of the present invention.

FIGS. 6, 7, and 8 depict exploded and cross sectional views of the horizontal handle assembly 50. FIGS. 6 and 7 show an exploded view of apparatus 20. In one embodiment, vertical body 33 and horizontal body 53 are a single piece, although various other embodiments contemplate the welding, brazing, adhesive, or mechanical fastening of two pieces into the approximate T-shape. Although what has been shown and described is a unitary body in an approximate T-shape, yet other embodiments of the present invention contemplate an arrangement of the vertical and horizontal bodies in an approximate L-shape.

Horizontal handle assembly 50 includes a threaded distal end 53d that includes within it a pocket 53c that retains a separate collet 54. Pocket 53c in one embodiment has a generally square cross sectional shape, which is complementary to the outer shape of the orienting section 54c of collet 54. Collet 54 is loosely retained within pocket 53c. The non-circular shapes of the pocket and the exterior of the collet are adapted and configured to prevent rotation of collet 54 relative to body 53.

Although collet 54 is readily and repeatedly insertable axially within pocket 53c, the axial retention of collet 54 within the pocket is provided by a retention mechanism 55. As best seen in FIGS. 6, 7, and 8, retention mechanism 55 includes a slide 55a that is received within a pocket 53e of body 53. A spring (not shown) located at the bottom of the pocket biases slide 55a upwards. Slide 55a includes a large central aperture through which collet 54 extends. At the bottom of the aperture is a protrusion 55b that is biased upward and received within a corresponding pocket 54b of collet 54. A spring 55c biases slide 55a upward into a position that restrains axial movement of collet 54.

FIGS. 6, 7, and 8 show the collet 54 in detail. The collet includes a non-circular orienting or driving section 54c on a proximal end. The distal end of collet 54 is generally tapered and circular in cross sectional shape, and fitting within an inner compression surface 57f of a compression assembly 57. Collet 54 includes a plurality of slits 54d that extend along much of the length of the collet. These slits reduce the tapered compression stiffness of the compressible diametral section 54a. Section 54a operates like a "chuck" to frictionally grasp a portion of the IM nail received within chucking portion 52b of the internal channel 52.

Referring to FIG. 8, tapered diametral section 54a is compressed as it is pulled into the inner diameter and inner compression surface 57f of compression assembly 57. Referring briefly to FIG. 6, compression assembly 57 includes a sliding compression member having a collar 57a and a flange 57b. A snap ring 57e retains the sliding compression member within a hand adjustable knob 56. In some embodiments, a plurality of ball bearings 57d reside within a raceway 57c and 56c between flange 57b and knob 56. In such embodiments, these balls and raceway provide a reduction in torque that would otherwise be passed from knob 56 to sliding compression member 57.

Although the use of balls in a raceway have been shown and described as one means for reducing the torque applied to the sliding compression member (which would likewise be transmitted by friction into collet 54), yet other embodiments of the present invention contemplate different means for appropriate handling of this friction. For example, in some embodiments a ball bearing assembly (inner and outer races, with balls in-between) or roller bearing assembly (inner and outer races with tapered rollers or needle bearings in-between) are contemplated. In still further embodiments, the torqueing interface between knob 56 and collar 57b includes low friction washers, such as metallic washers with low friction coatings or washers fabricated from low friction material that is hard enough and strong enough to accommodate the compressive load.

Knob 56 is threadably received onto horizontal body 53 by external threads 53d. Continued threaded engagement of knob 56 results in an axial force being applied through balls 57d onto flange 57b and collar 57a. Collar 57a includes an inner, tapered compressing surface 57f that is adapted and configured to slidingly engage the outer surface of compressible section 54a of collet 54. As the collar 57a moves axially (i.e., in a proximal direction), the inner diameter 52b of the internal channel is reduced until contact is achieved with the outer diameter of the IM nail. Further, threaded engagement of knob 56 results in increasing compression of the IM nail within section 54a, and thus an increased level of friction holding the IM nail in a fixed position. It can be seen that this radial compression onto the outer surface of the IM nail is accomplished by sliding of the tapered outer surface of diametral section 54a along an inner diametral surface 57f that is likewise tapered. However, yet other embodiments of the present invention contemplate only one of devices 54 or 57 having a tapered surface, and the other being relatively parallel with the axis of the gripped nail.

In yet other embodiments of the present invention, apparatus 52 is adapted and configured to receive a specific collet 54 chosen from a range of different size collets. Preferably, each collet within this group are adapted and configured for compression against different diameters of IM nails. The user selects a specific collet with a desired size of the diametral section 54a, removes the knob 56 and compression assembly 57 (which are held together by the snap ring 57e) from the distal end of body 53, which exposes the internal drive pocket 53c. The user then presses downward on slide 55a so as to lower protrusion 55b from the pocket 53c. With the slide depressed, the selected collet 54 can be dropped into the pocket 53c. By releasing slide 55a, the spring 55c pushes protrusion 55b into a position that axially locks collet 54 within body 53. The user then recouples knob 56 onto threads 53d, inserts the IM nail within slots 39 and 59 and through cavities 39c and 59c into internal channel 52 and out through exit 52a. Continued rotation of the knob results in a compressive force being applied to the IM nail that frictionally holds it in place.

FIGS. 9, 10, 11, and 12 show various views of an apparatus 120 according to another embodiment of the present invention. As previously noted, persons of ordinary skill in the art will recognize the various features of apparatus 120 that are applicable to apparatus 20, and vice versa. Apparatus 120 is similar to apparatus 20 previously shown and described, except for the differences that will now be discussed.

Bodies 133 and 153 are adapted and configured to be gripped by the hand of a user. Referring to FIGS. 9 and 10, it can be seen that vertical body 133 includes a plurality of ridges and finger grips 120a. Likewise, horizontal body 153 includes a plurality of ridges and finger grips 120a. Vertical handle 130 is adapted and configured to be gripped by the hand of a user, with the fingers extending around grips 120a and below base 153f of body 153 in lower portion 133b. The thumb of the user can be placed in a thumb depression 120b located at the top of body 133 and above base 153f in upper portion 133a.

In comparison to apparatus 20, it can be seen that apparatus 120 incorporates a shorter horizontal handle assembly 150 with a lesser number of finger grips (i.e. a combination of ridges and depressions), resulting in an overall horizontal length that is reduced relative to that of horizontal handle assembly 50. Still further, it can be seen that the vertical extent of vertical handle 130 is reduced relative to the vertical extent (or height) of horizontal handle 30. It can also be seen that the overall width of the upper section 133a of handle 130 is reduced relative to the width of upper section 33a of apparatus 20. It is understood that other embodiments of the present invention are not limited to the size and shape of apparatus 20 or 120, and contemplate still further embodiments in which the finger grips and thumb depression can be of any size and shape adapted and configured, either functionally or aesthetically, for a comfortable ergonomic fit in the hand of the user. Various embodiments of the present invention contemplate a range of lengths, widths, heights, number of finger grips, and shape of finger grips in order to provide the user with an orthopedic implant manipulation tool that is comfortable, light weight, and efficient to use.

These gripping features of vertical handle 30 are adapted and configured for manipulation by the user of an intramedullary nail extending out of channel exit 152a and extending into the bone of the recipient. Apparatus 120 further includes the gripping features 120a on body 153, which likewise facilitate manipulation of an intramedullary nail extending out of exit 152a and into the bone of the recipient. Various embodiments of the present invention contemplate an apparatus such as apparatus 120 that can maintain the medical implant (such as the IM nail) in a predetermined position or orientation (esp., relative to the recipient), which allowing the user to use either the horizontal body finger grips, or the vertical body finger grips.

Referring to FIGS. 11 and 12, it can be seen that apparatus 120 includes different apparatus and methods for compressing the diametral section 154a of collet 154 onto an IM nail (nail not shown). Apparatus 120 does not include the separate compression assembly 57 shown and disclosed for apparatus 20. Instead, the knob 156 incorporates an inner diameter 157a that is in sliding contact with the outer diameter of diametral section 154a. One or both of the inner diameter 157a or the outer diameter 154a can be tapered, such that the axial movement of knob 156 that occurs during rotation of threads 156b onto threads 153d results in relative axial movement between collet 154 and knob 156. This relative axial movement, because of the one or both tapered surfaces results in a decreased inner diameter in chucking section 152b. With sufficient rotation of knob 156, the diameter of chucking section 152b will reduce until sufficient compression is placed on the IM nail so as to frictionally hold it within collet 154.

Yet a further difference between apparatus 20 and 120 is with regards to the torqueing load path and torqueing magnitude imposed on collet 154 during rotation of knob 156. It can be seen that in some embodiments, such as apparatus 120, the ball bearings and/or low friction flat washer shown and described relative to apparatus 20 is not included. Therefore, as knob 156 is rotated relative to collet 154, there is both a radially inward applied compressive force as previously described, as well as a torque applied from inner diameter 157a to the outer diameter of section 154a. In some embodiments, this applied torque is structurally managed by the material selection for knob 156 and/or collet 154, such that there is an inherently a low friction interface. In still other embodiments, the inner diameter 157a or the outer diameter of section 154a can be coated with a low friction material. In still further embodiments, there can be a cylindrical (either straight cylinder or tapered cylinder) insert provided in knob 156, this insert being of a material and geometry adapted and configured for a low friction interface (insert not shown).

Figure 14:
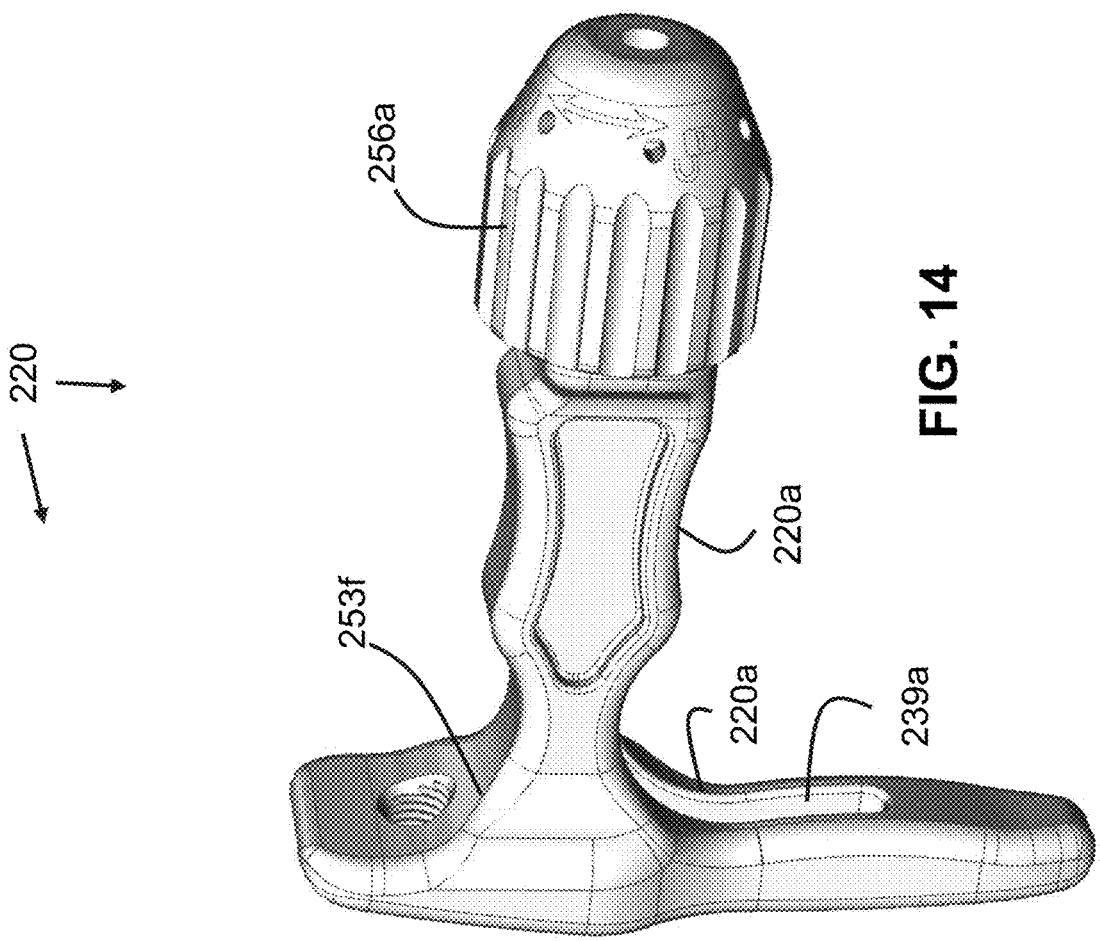
FIG. 14 is a side, distal perspective view of the apparatus of FIG. 13.
Figure 13:
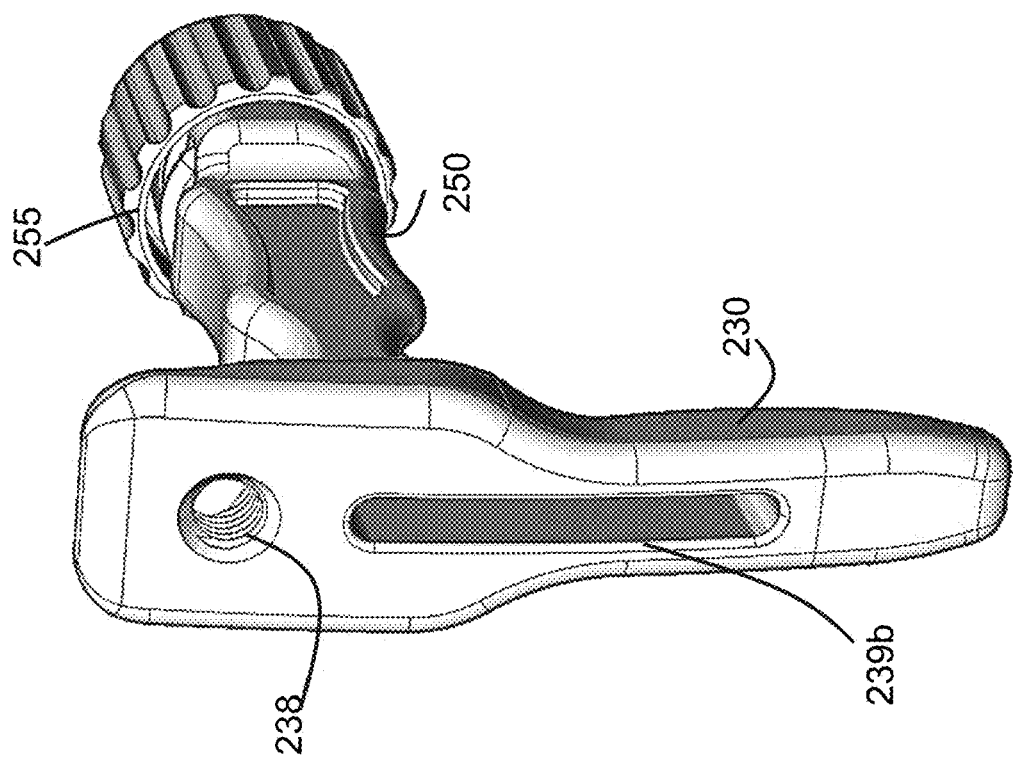
FIG. 13 is a side, proximal, perspective view of a shaded line drawing from a scaled CAD model of an apparatus according to another embodiment of the present invention.
Figure 15:
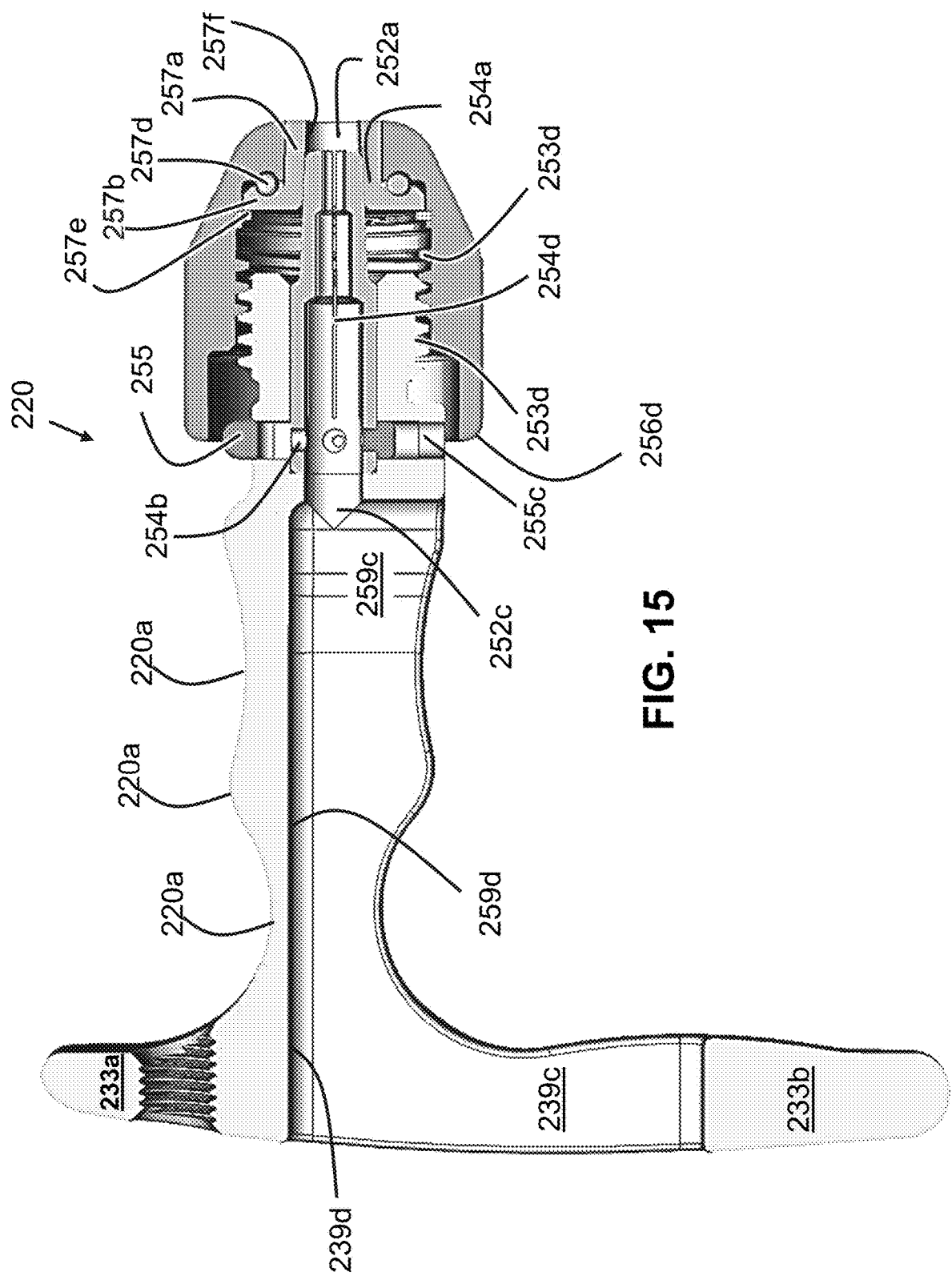
FIG. 15 is a side elevational cross sectional view of the apparatus of FIG. 13 as taken along the center line of the apparatus.

FIGS. 13, 14, and 15 show various views of an apparatus 220 according to yet another embodiment of the present invention. As previously noted, persons of ordinary skill in the art will recognize various features of apparatus 220 applicable to either apparatus 120 or apparatus 20, and vice versa. Apparatus 220 is similar in some respects to apparatus 20 previously shown and described, and similar in other respects to apparatus 120 as shown and described, except for the differences that will now be discussed.

Bodies 233 and 253 are adapted and configured to be gripped by the hand of a user. Referring to FIGS. 13 and 14, it can be seen that vertical body 233 includes a plurality of ridges and finger grips 220a. Likewise, horizontal body 253 includes a plurality of ridges and finger grips 220a. Vertical handle 230 is adapted and configured to be gripped by the hand of a user, with the fingers extending around grips 220a and below base 253f of body 253 in lower portion 233b.

In comparison to apparatus 20, it can be seen that apparatus 220 incorporates a shorter horizontal handle assembly 250 with a lesser number of finger grips (i.e. a combination of ridges and depressions), resulting in an overall horizontal length that is reduced relative to that of horizontal handle assembly 50. Still further, it can be seen that the vertical extent of vertical handle 230 is reduced relative to the vertical extent (or height) of horizontal handle 30. It can also be seen that the overall width of the upper section 233a of handle 230 is reduced relative to the width of upper section 33a of apparatus 20. It is understood that other embodiments of the present invention are not limited to the size and shape of apparatus 20 or 220, and contemplate still further embodiments in which the finger grips and thumb depression can be of any size and shape adapted and configured, either functionally or aesthetically, for a comfortable ergonomic fit in the hand of the user. Various embodiments of the present invention contemplate a range of lengths, widths, heights, number of finger grips, and shape of finger grips in order to provide the user with an orthopedic implant manipulation tool that is comfortable, light weight, and efficient to use.

These gripping features of vertical handle 30 are adapted and configured for manipulation by the user of an intramedullary nail extending out of channel exit 252a and extending into the bone of the recipient. Apparatus 220 further includes the gripping features 220a on body 253, which likewise facilitate manipulation of an intramedullary nail extending out of exit 252a and into the bone of the recipient. Various embodiments of the present invention contemplate an apparatus such as apparatus 220 that can maintain the medical implant (such as the IM nail) in a predetermined position or orientation (esp., relative to the recipient), which allowing the user to use either the horizontal body finger grips, or the vertical body finger grips.

Still further differences can be seen between apparatus 220 and apparatus 120 in comparing, respectively, FIGS. 13 to 9, and FIGS. 14 to 10. It is seen that apparatus 220 does not include a depression for the user's thumb. Still further, apparatus 220 includes a threaded through hole 238, in contrast to the blind threaded hole 38 of apparatus 20. Still further differences can be seen comparing the base 253f of the horizontal body 253 with the corresponding base sections 53f and 153f. It can be seen that base 253f on the lateral sides merges smoothly into the lateral sides of the vertical handle 230.

FIG. 15 shows a cross sectional cutaway, taken along the longitudinal axis, of apparatus 220. Horizontal handle assembly 250 includes a threaded distal end 253d that includes within it a pocket 253c that retains a separate collet 254. Pocket 253c in one embodiment has a generally square cross sectional shape, which is complementary to the outer shape of the orienting section 254c of collet 254. Collet 254 is loosely retained within pocket 253c. The non-circular shapes of the pocket and the exterior of the collet are adapted and configured to prevent rotation of collet 254 relative to body 253.

Although collet 254 is readily and repeatedly insertable axially within pocket 253c, the axial retention of collet 254 within the pocket is provided by a retention mechanism 255. Retention mechanism 255 includes a slide 255a that is received within a pocket 253e of body 253. A spring (not shown) located at the bottom of the pocket biases slide 255a upwards. Slide 255a includes a large central aperture through which collet 254 extends. At the bottom of the aperture is a protrusion 255b that is biased upward and received within a corresponding pocket 254b of collet 254. A spring 255c biases slide 255a upward into a position that restrains axial movement of collet 254.

The collet 254 includes a non-circular orienting or driving section 254c on a proximal end. The distal end of collet 254 is generally tapered and circular in cross sectional shape, and fitting within an inner compression surface 257f of a compression assembly 257. Collet 254 includes a plurality of slits 254d that extend along much of the length of the collet. These slits reduce the tapered compression stiffness of the compressible diametral section 254a. Section 254a operates like a "chuck" to frictionally grasp a portion of the IM nail received within chucking portion 252b of the internal channel 252.

Tapered diametral section 254a is compressed as it is pulled into the inner diameter and inner compression surface 257f of compression assembly 257. Compression assembly 257 includes a sliding compression member having a collar 257a and a flange 257b. A snap ring 257e retains the sliding compression member within a hand adjustable knob 256. In some embodiments, a plurality of ball bearings 257d reside within a raceway 257c and 256c between flange 257b and knob 256. In such embodiments, these balls and raceway provide a reduction in torque that would otherwise be passed from knob 256 to sliding compression member 257.

Knob 256 is threadably received onto horizontal body 253 by external threads 253d. Continued threaded engagement of knob 256 results in an axial force being applied through balls 257d onto flange 257b and collar 257a. Collar 257a includes an inner, tapered compressing surface 257f that is adapted and configured to slidingly engage the outer surface of compressible section 254a of collet 254. As the collar 257a moves axially (i.e., in a proximal direction), the inner diameter 252b of the internal channel is reduced until contact is achieved with the outer diameter of the IM nail. Further, threaded engagement of knob 256 results in increasing compression of the IM nail within section 254a, and thus an increased level of friction holding the IM nail in a fixed position. It can be seen that this radial compression onto the outer surface of the IM nail is accomplished by sliding of the tapered outer surface of diametral section 254a along an inner diametral surface 257f that is likewise tapered. However, yet other embodiments of the present invention contemplate only one of devices 254 or 257 having a tapered surface, and the other being relatively parallel with the axis of the gripped nail.

Still further differences of apparatus 220 are apparent by comparing FIG. 15 to either FIG. 4 or 11. In the embodiments 20 and 120, the channel 52/152 extends into an internal cavity 59c/159c. This cavity is shown to include an internal walls 59d/159d and 39d/159d that curve downward so as to be in slight interference with a straight nail being supported by the collet 54/154. As seen in FIG. 15, apparatus 220 does not include this feature, and instead the upper wall 259d, as well as the internal wall 239d, extend through horizontal handle 250 and vertical handle 230 so as to provide diametral clearance to a straight nail held within collet 254.

A still further different between apparatus 220 and the aforementioned apparatus 120 and 220 is in the covering, shielding, or shadowing of retention mechanism 255 by the proximal end 256d of knob 256. As shown in FIG. 15, when knob 256 is fully tightened and holding a nail within chuck 254, at least a portion of retention mechanism 255 is situated underneath the proximal edge 256d, and further extending into a cavity formed by the undersurface of knob 256. With this overlap or shadowing of mechanism 255, it is less likely that the user would inadvertently depress the top button surface of mechanism 255 during usage. However, an unscrewing of knob 256 not only releases the gripping of chuck 254 on the nail, but further moves the proximal surface 256d in a distal direction, such that the button surface of apparatus 255 becomes accessible when the collet 255 is loose.

Figure 16:
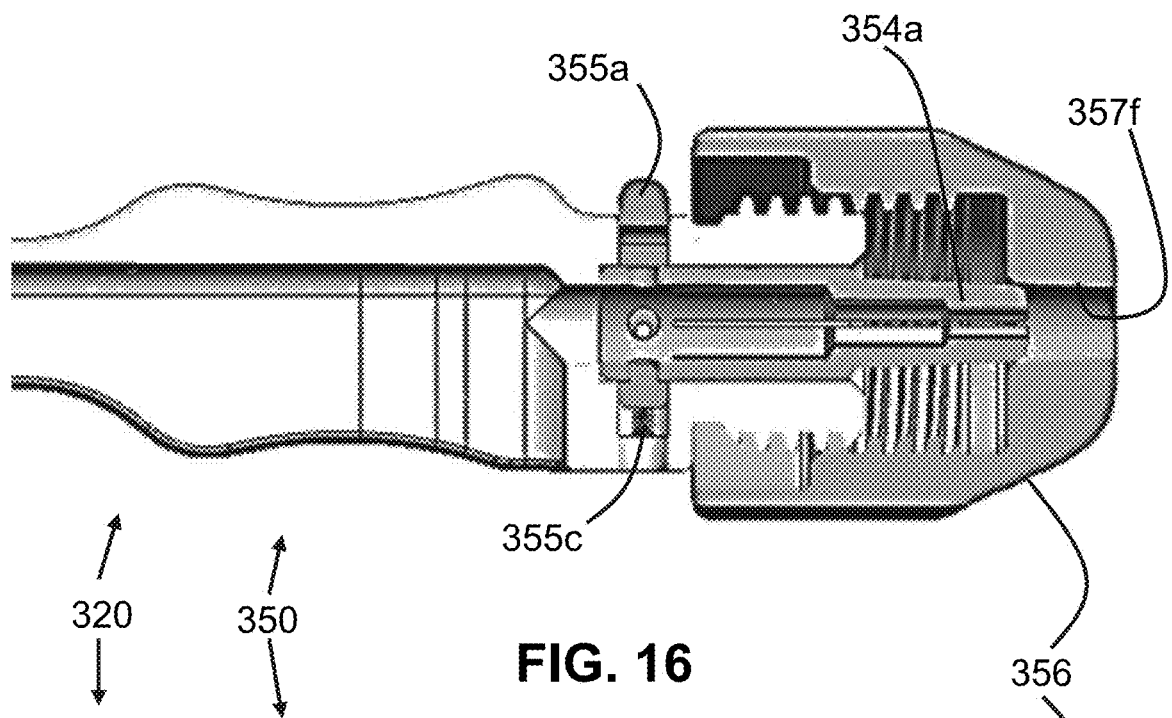
FIG. 16 is a side elevational cross sectional line drawing from a scaled CAD model of a portion of an apparatus according to another embodiment of the present invention.
Figure 17:
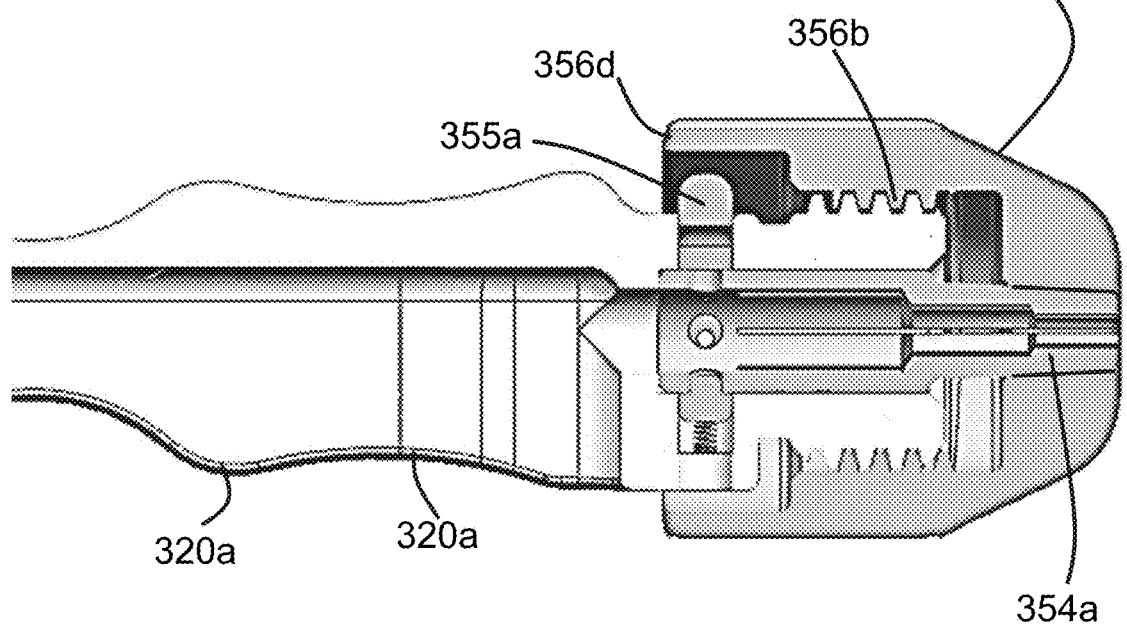
FIG. 17 is a view of the apparatus of FIG. 16 with the adjustment knob in a fully compressed position.
Figure 18:
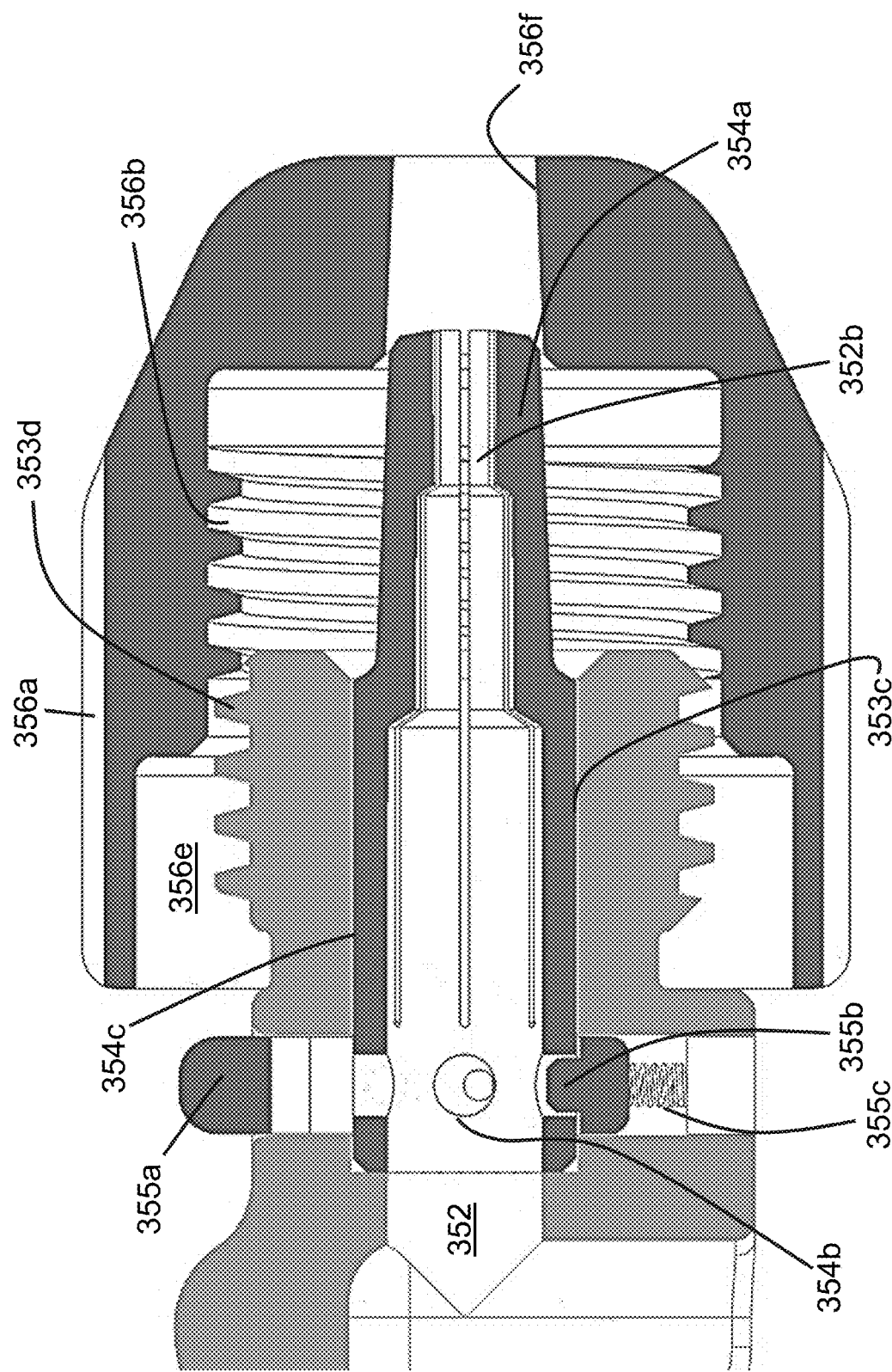
FIG. 18 is a close-up representation of a portion of the apparatus of FIG. 16.

FIGS. 16, 17, and 18 show various views of an apparatus 320 according to yet another embodiment of the present invention. Apparatus 320 is similar in some respects to apparatus 20 previously shown and described, and similar in other respects to apparatus 120 as shown and described, except for the differences that will now be discussed. Persons of ordinary skill in the art will recognize that many features of apparatus 320, 220, 120, and 20 are backward and forward compatible.

These figures each show a cross sectional cutaway, taken along the longitudinal axis, of apparatus 320. Horizontal handle assembly 350 includes a threaded distal end 353d that includes within it a pocket 353c that retains a separate collet 354. Pocket 353c in one embodiment has a generally square cross sectional shape with rounded corners, which is complementary to the outer shape of the orienting section 354c of collet 354. Collet 354 is loosely and slidably retained within pocket 353c. The non-circular shapes of the pocket and the exterior of the collet are adapted and configured to prevent rotation of collet 354 relative to body 353.

Although collet 354 is readily and repeatedly insertable axially within pocket 353c, the axial retention of collet 354 within the pocket is provided by a retention mechanism 355. Retention mechanism 355 includes a slide 355a that is received within a pocket 353e of body 353. A spring (not shown) located at the bottom of the pocket biases slide 355a upwards. Slide 355a includes a large central aperture through which collet 354 extends (similar to that shown in FIG. 6). At the bottom of the aperture is a protrusion 355b that is biased upward and received within a corresponding pocket 354b of collet 354. A spring 355c biases slide 355a upward into a position that restrains axial movement of collet 354.

The collet 354 includes a non-circular orienting or driving section 354c on a proximal end. The distal end of collet 354 is generally tapered and circular in cross sectional shape, and fitting within an inner compression surface 356f of knob 356. Collet 354 includes a plurality of slits 354d that extend along much of the length of the collet. These slits reduce the tapered compression stiffness of the compressible diametral section 354a. Section 354a operates like a "chuck" to frictionally grasp a portion of the IM nail received within chucking portion 352b of the internal channel 352. Tapered diametral section 354a is compressed as it is pulled into the inner diameter and inner compression surface 356f of knob 56.

Knob 356 is threadably received onto horizontal body 353 by external threads 353d. Continued threaded engagement of knob 356 results in an axial force being applied along the surface of collet 354. Knob 356 includes an inner, tapered compressing surface 356f that is adapted and configured to slidingly engage the outer surface of compressible section 354a of collet 354. As the knob 356 moves axially (i.e., in a proximal direction), the inner diameter 352b of the internal channel is reduced until contact is achieved with the outer diameter of the IM nail. Further, threaded engagement of knob 356 results in increasing compression of the IM nail within section 354a, and thus an increased level of friction holding the IM nail in a fixed position. It can be seen that this radial compression onto the outer surface of the IM nail is accomplished by sliding of the tapered outer surface of diametral section 354a along an inner diametral surface 356f that is likewise tapered. However, yet other embodiments of the present invention contemplate only one of devices 354 or 356 having a tapered surface, and the other being relatively parallel with the axis of the gripped nail.

Apparatus 320 provides a covering, shielding, or shadowing of retention mechanism 355 by the proximal end 356d of knob 356. As shown in FIG. 17, when knob 356 is fully tightened and holding a nail within chuck 354, retention mechanism 355 is situated underneath the proximal edge 356d, and further extending into a cavity 356e formed by the undersurface of knob 356. With this shielding of mechanism 355, it is less likely that the user would inadvertently depress the top button surface of mechanism 355 during usage. However, an unscrewing of knob 356 not only releases the gripping of chuck 354 on the nail, but further moves the proximal surface 356d in a distal direction, such that the button surface of apparatus 355 becomes accessible when the collet 355 is loose.

What has been shown and described herein is a tool or instrument for manipulation of an orthopedic implant. Various configurations of ergonomic features are shown to provide efficient, accurate, reliable use by a user such as an orthopedic surgeon. These various hand-adapted features, such as finger grips and thumb depressions, can be of a wide variety of shapes and sizes. For example, some finger grips include depressions that are separated by relatively sharp ridges, whereas other finger depressions are separated by gently rounded ridges, as one example. As another example, a feature adapted and configured for placement of the user's thumb can be a simple depression for placement of the thumb which can be relatively wide and shallow, or relatively narrow and sharp. Still further, the thumb-fitting feature may provide for placement of only the flat of the thumb, or may be adapted to receive a thumb that overlaps the top of the depression, such as a ridge adapted and configured to be placed in a joint of the thumb.

It is understood by those of ordinary skill in the art that these hand-accommodating features can have a decidedly aesthetic value, such that a user selects a hand held instrument not only for the various functions of the instrument, but further for the look and shape of the hand-accommodating features. It is understood that the finger grips and thumb depressions shown and described herein are but one aesthetic expression of such features, and that various embodiments of the present invention contemplate other aesthetically pleasing hand-accommodating features.

Various aspects of different embodiments of the present invention are expressed in paragraphs X1, X2, and X3 as follows:

X1. One aspect of the present invention pertains to an apparatus for manipulation of an intramedullary nail. The apparatus preferably includes a first member and a second member defining a channel for passage therein of an intramedullary nail. The apparatus preferably includes the second member having a proximal side and a distal side and including a second handle. The apparatus preferably includes the first member including a first handle having a length and having at least one of a finger-sized ridge or finger-sized depression to accommodate therewith the fingers of the hand of a user, the first member being fixedly attached to the distal side of the second member such that the first handle and second handle are arranged in a T-shape, offset T-shape, or L-shape, the first member preferably including a pocket; and a collet having an elastically compressible section proximate internal channel for coupling to a portion of an intramedullary nail within the compressible diametral section, the collet preferably being received within the pocket.

X2. Another aspect of the present invention pertains to an apparatus for manipulation of an intramedullary nail. The apparatus preferably includes a horizontal handle assembly and a vertical handle defining an internal channel for passage therethrough of an intramedullary nail. The apparatus preferably includes the vertical handle having a proximal side and a distal side and being adapted and configured to be gripped by the hand of a user, the vertical handle including a slotted entrance to the internal channel. The apparatus preferably includes the horizontal handle assembly extending from the distal side of the vertical handle and being adapted and configured to be gripped by the hand of a user, the horizontal handle including an exit therein from the internal channel and a collet having a compressible diametral section surrounding the exit of the internal channel for frictional coupling to a first linear portion of an intramedullary nail within the compressible diametral section.

X3. Yet another aspect of the present invention pertains to an apparatus for manipulation of an intramedullary nail. The apparatus preferably includes a first member and a second member defining an internal channel having an exit for passage therethrough of an intramedullary nail. The apparatus preferably includes the second member having a proximal side and a distal side and including a handle adapted and configured to be gripped by the hand of a user. The apparatus preferably includes the first member extending from the distal side of the second member in an approximate T-shape and including a handle adapted and configured to be gripped by the hand of a user, the first handle defining an internal pocket. The apparatus preferably includes a collet having a compressible diametral section surrounding the exit of the internal channel for frictional coupling to a first portion of an intramedullary nail within the compressible diametral section; and a retention mechanism that can be configured to retain the collet within the pocket or to remove the collet from the pocket.

Yet other embodiments pertain to any of the previous statements X1, X2, or X3, which are combined with one or more of the following other aspects. It is also understood that any of the aforementioned X paragraphs include listings of individual features that can be combined with individual features of other X paragraphs.

Wherein the horizontal handle assembly defines a pocket that receives the collet, and which further comprises a two position retention mechanism having a first position that axially retains the collet within the pocket and a second position that permits axial removal of the collet from the pocket.

Wherein the retention mechanism includes a pushbutton, and pressing of the pushbutton permits removal of the collet from the pocket.

Wherein the retention mechanism is biased to the first position.

Wherein the pocket has a non-circular internal shape and the collet has a complementary non-circular shape.

Wherein at least one of the vertical (second) handle or the horizontal (first) handle assembly includes a through slot providing access into the cavity and adapted and configured to receive therethrough a third portion of the frictionally coupled nail.

Wherein the through slot extends from the proximal side of the vertical (second) handle to the distal side of the vertical handle.

Wherein the horizontal (first) handle assembly has a top and a bottom, and the through slot extends through the bottom.

Wherein the horizontal handle assembly has a top and a bottom, and the through slot extends through the bottom.

Wherein the cavity includes an internal wall, the compressible diametral section defines a cylinder intersecting the wall, and the internal wall intersects less than the full cross sectional area of the cylinder.

Wherein at least one of the vertical handle or the horizontal handle includes an internal cavity adapted and configured for receiving therein a second non-linear portion of the intramedullary nail when the first portion is frictionally coupled to the collet.

Wherein the compressible diametral section has a centerline, and the slotted entrance extends for a length, and a portion of the length is offset from the centerline.

Wherein the horizontal handle assembly has a base that extends to the vertical handle and the vertical handle includes a threaded coupling on the proximal side located generally opposite of the base.

Which further comprises a rotatable hand-adjustable knob, wherein the knob is threadably coupled to the horizontal handle assembly and the collet is received within the horizontal handle, and rotation of the knob changes the frictional force applied by the compressible diametral section to the intramedullary nail.

Which further comprises a hand-adjustable knob, and wherein the knob and the collet are located at the distal end of the horizontal handle, and adjustment of the knob changes the compression applied to the intramedullary nail by the compressible diametral section.

Which further comprises a rotatable hand-adjustable knob, wherein the knob is threadably coupled to the horizontal handle assembly and the collet is non-rotatably received within the horizontal handle, and which further comprises an axially sliding compression member surrounding the distal portion of the collet.

Wherein rotation of the knob in a direction drives the sliding compression member to move relative to the collet and increase the frictional force applied by the compressible diametral section to the intramedullary nail.

Wherein rotation of the knob in a direction drives the sliding compression member to move axially relative to the collet and the knob drives the compression member with ball bearings.

Wherein the vertical (second) handle includes a wider section generally above and opposite the horizontal (first) handle assembly, and a narrower portion extending below the wider portion, the proximal side of the wider portion being adapted and configured for receiving hammering impacts to drive an intramedullary nail in the internal channel in a distal direction.

Wherein the distal side of the horizontal handle assembly is adapted and configured for receiving hammering impacts to pull an intramedullary nail in the internal channel in a proximal direction.

Wherein the horizontal (first) handle assembly has an underside and the vertical (second) handle has a top surface, and the horizontal handle assembly includes a second handle adapted and configured to extend from the distal side of the vertical handle such that the fingers of the user can wrap around the vertical handle and under the second handle and the thumb of the user can wrap over the top surface.

Wherein the vertical handle has top, bottom, and middle, with the bottom including grooves adapted and configured to gripping by the fingers of a user, the top has a groove adapted and configured for receiving the thumb of the user, and the horizontal handle extends from the middle.

Wherein the horizontal handle assembly includes gripping features adapted and configured for gripping by the fingers of a user.

Wherein the vertical handle includes gripping features adapted and configured for gripping by the fingers of a user.

Wherein the vertical handle and horizontal handle assembly form an approximate T-shape.

Wherein the vertical handle and horizontal handle assembly form an offset T-shape.

Wherein the horizontal handle assembly includes a second handle and the vertical handle and the second handle are a unitary piece.

Which further comprises a two position retention mechanism having a retaining position that axially retains the collet within the pocket and a removal position that permits removal of the collet from the pocket, and a rotatable hand-adjustable knob having an interior, wherein rotation of the knob to a first position maximizes the frictional force applied by the compressible diametral section to the intramedullary nail, and in the first position the knob limits access to the pushbutton.

Which further comprises a retention mechanism including a pushbutton, wherein pressing of the pushbutton permits removal of the collet from the pocket, and a rotatable knob having an interior, wherein rotation of the knob to a position moves the knob such that at least a portion of the knob is located within the interior.

Wherein the collet is one of a plurality of collets provided in a kit, each the collet being adapted and configured to accept therein a different predetermined diameter of intramedullary nail, selected from a plurality of different sized intramedullary nails, wherein each of the collets have the same shape of driven section for receipt within a predetermined size of driving pocket or retention pocket in the first member, the pocket having a shape complementary to the common shape of the driven sections.

Wherein both the first handle and the second handle are ergonomically adapted and configured to be gripped by the hand of a user from either of two hand positions for the same predetermined orientation of the internal channel.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. An apparatus for manipulation of an intramedullary nail, the apparatus comprising:
    a first member defining an internal channel for passage therethrough of the intramedullary nail, the channel having an exit;
    a second member having a proximal side and a distal side and including a handle adapted and configured to be gripped by a hand of a user, the handle having at least one feature adapted and configured to receive thereon a finger of the hand of the user, a proximal end of said first member being fixedly attached to the distal side of the second member, the first member extending in a distal direction from the second member, said first member defining an internal pocket;
    a collet having a compressible diametral section surrounding the exit of the internal channel for frictional coupling to a first portion of the intramedullary nail within the compressible diametral section, a portion of said collet being received within the pocket;
    a two position retention mechanism having a first position that retains said collet within the pocket and a second position that permits removal of said collet from said pocket; and
    a rotatable hand-adjustable knob having an interior,
    wherein rotation of said knob to a compressing position maximizes a frictional force applied by the compressible diametral section to the intramedullary nail, and
    wherein said knob is threadably coupled to said first member assembly and said collet is unable to rotate when received within the pocket.

2. An apparatus for manipulation of an intramedullary nail, the apparatus comprising:

a first member defining an internal channel for passage therethrough of the intramedullary nail, the channel having an exit;

a second member having a proximal side and a distal side and including a handle adapted and configured to be gripped by a hand of a user, the handle having at least one feature adapted and configured to receive thereon a finger of the hand of the user, a proximal end of said first member being fixedly attached to the distal side of the second member, the first member extending in a distal direction from the second member, said first member defining an internal pocket;

a collet having a compressible diametral section surrounding the exit of the internal channel for frictional coupling to a first portion of the intramedullary nail within the compressible diametral section, a portion of said collet being received within the pocket;

a two position retention mechanism having a first position that retains said collet within the pocket and a second position that permits removal of said collet from said pocket;

a rotatable hand-adjustable knob having an interior; and an axially sliding compression member surrounding a distal portion of said collet, wherein rotation of said knob to a compressing position maximizes a frictional force applied by the compressible diametral section to the intramedullary nail, and wherein rotation of said knob toward the compressing position drives said sliding compression member to move relative to said collet.

3. The apparatus of claim 2, wherein said knob drives said compression member with ball bearings.

4. An apparatus for manipulation of an intramedullary nail, the apparatus comprising:

a first member defining an internal channel for passage therethrough of the intramedullary nail, the channel having an exit;

a second member having a proximal side and a distal side and including a handle adapted and configured to be gripped by a hand of a user, the handle having at least one feature adapted and configured to receive thereon a finger of the hand of the user, a proximal end of said first member being fixedly attached to the distal side of the second member, the first member extending in a distal direction from the second member, said first member defining an internal pocket;

a collet having a compressible diametral section surrounding the exit of the internal channel for frictional coupling to a first portion of the intramedullary nail within the compressible diametral section, a portion of said collet being received within the pocket; and a two position retention mechanism having a first position that retains said collet within the pocket and a second position that permits removal of said collet from said pocket, wherein the exit has a central axis, and the proximal end of said first member extends in the distal direction from said second member, with a first portion of a length of said second member extending on one side of the central axis and a second portion of a length of said second member extending on an opposing side of the central axis, and wherein one of a first portion of the second member or a second portion of the second member includes a threaded hole having an axis generally parallel to the central axis of the exit.

5. An apparatus for manipulation of an intramedullary nail, the apparatus comprising:

a first member defining an internal channel for passage therethrough of the intramedullary nail, the channel having an exit;

a second member having a proximal side and a distal side and including a handle adapted and configured to be gripped by a hand of a user, the handle having at least one feature adapted and configured to receive thereon a finger of the hand of the user, a proximal end of said first member being fixedly attached to the distal side of the second member, the first member extending in a distal direction from the second member, said first member defining an internal pocket;

a collet having a compressible diametral section surrounding the exit of the internal channel for frictional coupling to a first portion of the intramedullary nail within the compressible diametral section, a portion of said collet being received within the pocket; and a two position retention mechanism having a first position that retains said collet within the pocket and a second position that permits removal of said collet from said pocket, wherein the exit has a central axis, and the proximal end of said first member extends in the distal direction from said second member, with a first portion of a length of said second member extending on one side of the central axis and a second portion of a length of said second member extending on an opposing side of the central axis, and wherein a threaded hole extends through both the distal and proximal sides of the portion of said second member.

6. An apparatus for manipulation of an intramedullary nail, comprising:

a horizontal handle having an internal channel for passage therethrough of the intramedullary nail, the channel having an exit;

a vertical handle having an elongate entrance for the internal channel, said vertical handle having a proximal side and a distal side and including a plurality of features adapted and configured for gripping by a hand of a user; the horizontal handle extending from the distal side of the vertical handle and being adapted and configured to be gripped by the hand of the user;

a collet having a compressible diametral section surrounding a portion of the internal channel for frictional coupling to a first portion of the intramedullary nail within the compressible diametral section;

a hand-adjustable knob having an interior; and a retention mechanism adapted and configured for releasing said collet from said horizontal handle, wherein the elongate entrance, the internal channel, and the exit are adapted and configured to receive therein a second curving portion of the intramedullary nail, wherein adjustment of said knob changes a frictional force by said collet to the intramedullary nail, wherein said collet is releasably coupled to said horizontal handle, and wherein said knob limits access by the user to the retention mechanism, and wherein one of a first portion of the vertical handle or a second portion of the vertical handle includes a threaded hole having an axis generally parallel to a central axis of the exit.

7. An apparatus for manipulation of an intramedullary nail, the apparatus comprising:

a horizontal handle having an internal channel for passage therethrough of the intramedullary nail, the channel having an exit;

a vertical handle having an elongate entrance for the internal channel, said vertical handle having a proximal side and a distal side and including a plurality of features adapted and configured for gripping by a hand of a user; the horizontal handle extending from the distal side of the vertical handle and being adapted and configured to be gripped by the hand of the user;

a collet having a compressible diametral section surrounding a portion of the internal channel for frictional coupling to a first portion of the intramedullary nail within the compressible diametral section;

a hand-adjustable knob having an interior; and a retention mechanism adapted and configured for releasing said collet from said horizontal handle, wherein the elongate entrance, the internal channel, and the exit are adapted and configured to receive therein a second curving portion of the intramedullary nail, wherein adjustment of said knob changes a frictional force by said collet to the intramedullary nail, wherein said collet is releasably coupled to said horizontal handle, and wherein said knob limits access by the user to the retention mechanism, and wherein a threaded hole extends through both the distal and proximal sides of the portion of the vertical handle.

8. An apparatus for manipulation of an intramedullary nail, the apparatus comprising:

a first handle including an internal channel for passage therein of the intramedullary nail, the channel having an exit with a central axis;

a second handle having a proximal side and a distal side and including a plurality of features adapted and configured for gripping by a hand of a user;

said first handle having at least one of a finger-sized ridge or finger-sized depression to accommodate therewith the hand of the user, a proximal end of said first handle extending fixedly in a distal direction from the distal side of said second handle such that the first handle and second handle are arranged in an approximate T-shape, with a first portion of a length of said second handle extending on one side of the internal channel of said first handle and a second portion of a length of said second handle extending on an opposing side of the internal channel of said first handle; and a collet having a section proximate to the exit of the internal channel that is adapted and configured for adjustable coupling to a portion of the intramedullary nail within the collet, wherein said second handle includes a threaded hole having an axis generally parallel to the central axis of the exit.

* * * * *